(12) United States Patent
Kompala

(10) Patent No.: US 10,576,399 B2
(45) Date of Patent: Mar. 3, 2020

(54) PARTICLE SETTLING DEVICES

(71) Applicant: Dhinakar S. Kompala, Superior, CO (US)

(72) Inventor: Dhinakar S. Kompala, Superior, CO (US)

(73) Assignee: SUDHIN BIOPHARMA, Superior, CO (US)

(*) Notice: Subject to any disclaimer, the term of this patent is extended or adjusted under 35 U.S.C. 154(b) by 0 days.

(21) Appl. No.: 16/375,683

(22) Filed: Apr. 4, 2019

(65) Prior Publication Data

US 2019/0321756 A1 Oct. 24, 2019

Related U.S. Application Data

(60) Provisional application No. 62/659,295, filed on Apr. 18, 2018.

(51) Int. Cl.
*B01D 21/26* (2006.01)
*B04C 5/10* (2006.01)
(Continued)

(52) U.S. Cl.
CPC ....... *B01D 21/265* (2013.01); *B01D 21/0045* (2013.01); *B01J 8/007* (2013.01);
(Continued)

(58) Field of Classification Search
CPC ............. B01D 21/265; B01D 21/0045; B01D 17/0211; B01D 17/0214; B01D 17/0217;
(Continued)

(56) References Cited

U.S. PATENT DOCUMENTS 1,602,935 A * 10/1926 Rasey ................ B01D 17/0211
210/223
2,230,386 A * 2/1941 Pecker ............... B01D 21/0018
210/521
(Continued)

FOREIGN PATENT DOCUMENTS

DE 4438510 4/1996
EP 521583 * 7/1993 .......... B01D 17/028
(Continued)

OTHER PUBLICATIONS

U.S. Appl. No. 16/099,248, filed Nov. 6, 2018, Kompala.
(Continued)

*Primary Examiner* — Joseph W Drodge
(74) *Attorney, Agent, or Firm* — Sheridan Ross PC

(57) ABSTRACT

Settling devices for separating particles from a bulk fluid with applications in numerous fields. The particle settling devices include a first stack of cones with a small opening oriented upwardly or downwardly. Optionally, the settling devices may include a second stack of cones with a small opening oriented downwardly or upwardly. The cones may be concave or convex. These devices are useful for separating small (millimeter or micron sized) particles from a bulk fluid with applications in numerous fields, such as biological (microbial, mammalian, plant, insect or algal) cell cultures, solid catalyst particle separation from a liquid or gas and waste water treatment.

23 Claims, 17 Drawing Sheets

(51) Int. Cl.
| | |
|---|---|
| *B01D 21/00* | (2006.01) |
| *C02F 1/38* | (2006.01) |
| *B01J 8/00* | (2006.01) |
| *C07K 1/22* | (2006.01) |
| *C12M 1/00* | (2006.01) |
| *C12M 1/26* | (2006.01) |
| *B04C 5/103* | (2006.01) |
| *C02F 103/34* | (2006.01) |

(52) U.S. Cl.
CPC ............. *B01J 8/0055* (2013.01); *B04C 5/103* (2013.01); *C02F 1/38* (2013.01); *C07K 1/22* (2013.01); *C12M 29/10* (2013.01); *C12M 33/22* (2013.01); *C12M 47/10* (2013.01); *B01J 2208/00761* (2013.01); *C02F 2103/34* (2013.01)

(58) Field of Classification Search
CPC ............... B01D 17/21; B01D 17/0039; B01D 17/0045; B01D 17/0048; B01D 17/0069; B01D 17/26; B01D 17/265; B01D 17/267; B01D 17/30; B01D 17/305; B01D 17/32; C12M 47/10; C12M 33/22; C12M 29/10; C12M 41/00; C12M 47/02; C12M 33/10; C12M 45/05; C12M 47/04; C12M 47/12; B04C 5/103; B04C 3/00; B04C 3/04; B04C 9/00; B04C 11/00; B04C 2009/004; C07K 1/22; C07K 1/14; C07K 16/00; C02F 1/38; C02F 2103/34; C02F 1/385; C02F 2101/30; C02F 2103/32; C02F 2103/343; B01J 2208/00761; B01J 8/0055; B01J 8/007; C12N 5/0636; C12N 5/04; C12N 7/00; C12N 1/02; C12N 5/0662; C12N 5/0644; C12N 1/16; C12N 1/12; C12Q 3/00; Y02W 10/37
USPC ....... 210/739, 742, 743, 745, 787, 788, 800, 210/804, 85, 94, 96.1, 143, 149, 512.1, 210/512.2, 512.3, 522
See application file for complete search history.

(56) References Cited

U.S. PATENT DOCUMENTS

| | | | | |
|---|---|---|---|---|
| 2,261,101 A * | 10/1941 | Erwin | ..................... | E21B 43/34 126/355.1 |
| 2,307,154 A * | 1/1943 | Osuna | ................ | B01D 21/0003 127/13 |
| 2,651,415 A * | 9/1953 | Worthen | ............ | B01D 17/0211 210/93 |
| 3,337,050 A * | 8/1967 | Labecki | .................... | B04C 5/14 209/731 |
| 3,718,257 A * | 2/1973 | Bach | .................. | B01D 21/0024 210/802 |
| 3,960,734 A | 6/1976 | Zagorski | | |
| 4,048,069 A | 9/1977 | Cuvillier et al. | | |
| 4,151,084 A | 4/1979 | Probstein | | |
| 4,348,215 A * | 9/1982 | Dehne | ....................... | B04C 5/28 209/711 |
| 4,939,087 A * | 7/1990 | Van Wie | ............... | B04B 5/0442 210/651 |
| 5,401,404 A * | 3/1995 | Strauss | ............. | B01D 17/0208 210/265 |
| 5,492,622 A * | 2/1996 | Broussard | .......... | B01D 17/0205 209/728 |
| 5,624,580 A | 4/1997 | De Hoxar | | |
| 5,817,505 A | 10/1998 | Thompson et al. | | |
| 5,840,198 A * | 11/1998 | Clarke | ............... | B01D 17/0211 210/802 |
| 5,904,855 A * | 5/1999 | Manz | ................. | B01D 21/0003 210/709 |
| 5,948,271 A * | 9/1999 | Wardwell | ................. | B04B 1/20 210/143 |
| 6,133,019 A * | 10/2000 | Herman | ................. | C12M 27/10 435/286.1 |
| 6,146,891 A * | 11/2000 | Condon | ............... | C12N 5/0075 435/235.1 |
| 6,720,358 B2 | 4/2004 | Espinoza et al. | | |
| 7,078,439 B2 | 7/2006 | Odueyungbo et al. | | |
| 7,431,846 B2 | 10/2008 | Palmer | | |
| 7,931,445 B2* | 4/2011 | Haans | ................... | F03D 1/0608 416/1 |
| 8,216,854 B2 | 7/2012 | Ballerstadt et al. | | |
| 8,728,318 B2 | 5/2014 | Vellinga et al. | | |
| 2003/0136729 A1* | 7/2003 | Batson | ............... | B01D 17/0211 210/512.1 |
| 2005/0194316 A1* | 9/2005 | Pourahmadi | ...... | B01L 3/502715 210/638 |
| 2005/0194322 A1 | 9/2005 | Palmer | | |
| 2006/0032486 A1 | 2/2006 | Prasad | | |
| 2007/0246431 A1* | 10/2007 | Palmer | ............... | B01D 21/0045 210/715 |
| 2008/0290023 A1* | 11/2008 | Greene | ............. | B01D 21/2444 210/512.1 |
| 2009/0159523 A1 | 6/2009 | McCutchen | | |
| 2011/0097800 A1 | 4/2011 | Kauling et al. | | |
| 2012/0180662 A1 | 7/2012 | Missalla et al. | | |
| 2013/0052105 A1 | 2/2013 | Butler | | |
| 2013/0272943 A1* | 10/2013 | Braga | .................... | B01D 53/00 423/242.2 |
| 2014/0011270 A1 | 1/2014 | Chotteau et al. | | |
| 2014/0044696 A1 | 2/2014 | Bamdad | | |
| 2014/0225286 A1 | 8/2014 | Paxton | | |
| 2014/0243571 A1* | 8/2014 | Lyon | ...................... | E21B 43/34 585/800 |
| 2017/0090490 A1* | 3/2017 | Mills | ................ | G05B 19/41865 |
| 2017/0197158 A1 | 7/2017 | Kompala | | |
| 2017/0333815 A1 | 11/2017 | Kompala | | |

FOREIGN PATENT DOCUMENTS

| | | |
|---|---|---|
| GB | 105318 | 4/1917 |
| RU | 2182508 | 5/2002 |
| WO | WO 91/06627 | 5/1991 |

OTHER PUBLICATIONS

Batt et al., "Inclined Sedimentation for Selective Retention of Viable Hybridomas in a Continuous Suspension Bioreactor," Biotechnology Progress, 1990, vol. 6, pp. 458-464, abstract only, 3 pages.
Boycott, "Sedimentation of Blood Corpuscles," Nature, 1920, vol. 104(2621), pp. 532, abstract only, 1 page.
Brennan et al., "A perfusion system for antibody production by shear-sensitive hybridoma cells in a stirred reactor," Biotechnol. Techniques, 1987, vol. 1(3), pp. 169-174, abstract only, 5 pages.
Bungay et al., "Cross-Flow Lamellar Settlers for Microbial Cells," Biotechnology and Bioengineering, 1984, vol. 26, pp. 640-641.
Cilliers et al., "The application of mini-gydrocyclones in the concentration of yeast suspensions," Chemical Engineering Journal, 1997, vol. 65(1), pp. 21-26, abstract only, 2 pages.
Elsayed et al., "Use of Hydrocyclones for Mammalian Cell Retention: Separation Efficiency and Cell Viability (Part 1)," Eng. Life Sci., 2006, vol. 6(4), pp. 347-354.
Geiler, et al., "Genetically Engineered in Vitro Erythropoiesis," International Journal of Stem Cells, 2016, vol. 9(1), pp. 53-59.
Gorenflo et al., "Optimization of an Acoustic Cell Filter with a Novel Air-Backflush System," Biotechnology Progress, 2003, vol. 19, pp. 30-36, abstract only, 2 pages.
Himmelfarb et al., "Spin Filter Culture: The Propagation of Mammalian Cells in Suspension" Science, 1969, vol. 164(3879), pp. 555-557, abstract only, 1 page.
Johnson et al., "Use of the Centritech Lab Centrifuge for Perfusion Culture of Hybridoma Cells in Protein-Free Medium," Biotechnology Progress, 1999, vol. 12, pp. 855-864, abstract only, 1 page.

(56) References Cited

OTHER PUBLICATIONS

Kitano et al., "Production of human monoclonal antibodies by heterohybridomas," Applied Microbiology and Biotechnology, 1986, vol. 24(4), pp. 282-286, abstract only, 1 page.

Knazek et al., "Cell culture on artificial capillaries: an approach to tissue growth in vitro," 1972, vol. 178(4056), pp. 65-67, abstract only, 1 page.

Panuganti et al., "Three-Stage Ex Vivo Expansion of High-Ploidy Megakaryocytic Cells: Toward Large-Scale Platelet Production," Tissue Engineering Part A, 2013, vol. 19(7&8), pp. 998-1014.

Searles et al., "Viable Cell Recycle with an Inclined Settler in the Perfusion Culture of Suspended Recombinant Chinese Hamster Ovary Cells," Biotechnology Progress, 1994, vol. 10(2), pp. 198-206, abstract only, 1 page.

Yuan et al., "An Investigation into the Possible Use of Hydrocyclones for the Removal of Yeast from Beer," Bioseparation, 1996, vol. 6, pp. 159-163, abstract only, 1 page.

International Search Report and Written Opinion for International (PCT) Patent Application No. PCT/US15/39723, dated Dec. 1, 2015, 14 pages.

International Preliminary Report on Patentability for International (PCT) Patent Application No. PCT/US15/39723, dated Jan. 10, 2017, 10 pages.

International Search Report and Written Opinion for International (PCT) Patent Application No. PCT/US15/63195, dated Feb. 12, 2016, 12 pages.

International Preliminary Report on Patentability for International (PCT) Patent Application No. PCT/US15/63195, dated Jun. 6, 2017, 9 pages.

International Search Report and Written Opinion for International (PCT) Patent Application No. PCT/US17/31252, dated Jul. 20, 2017, 8 pages.

International Search Report and Written Opinion for International (PCT) Patent Application No. PCT/US19/25884, dated Jul. 30, 2019 10 pages.

Official Action for U.S. Appl. No. 15/586,902, dated Jul. 10, 2019 18 pages.

Official Action for U.S. Appl. No. 16/099,248, dated Jul. 10, 2019 17 pages.

* cited by examiner

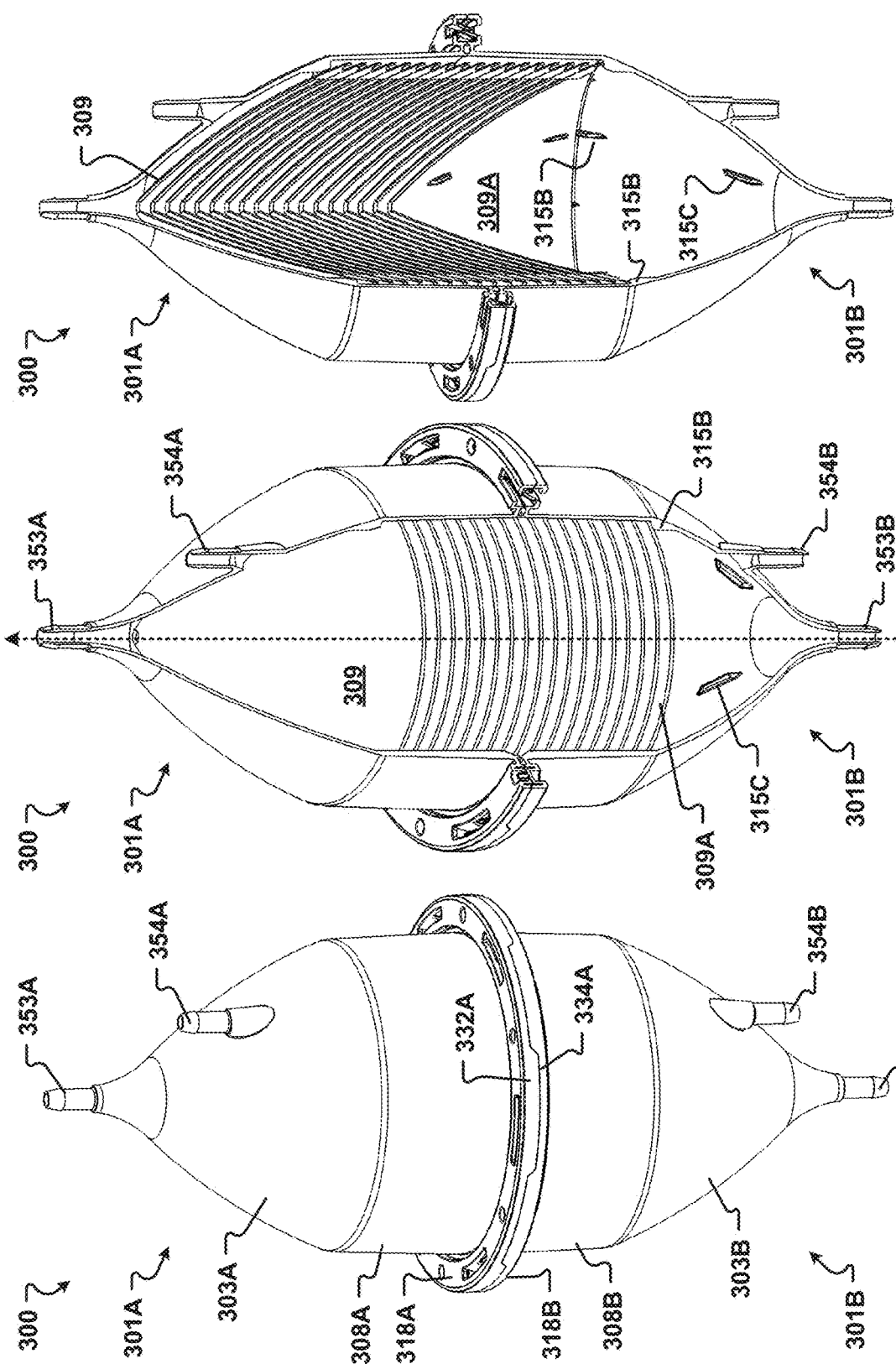

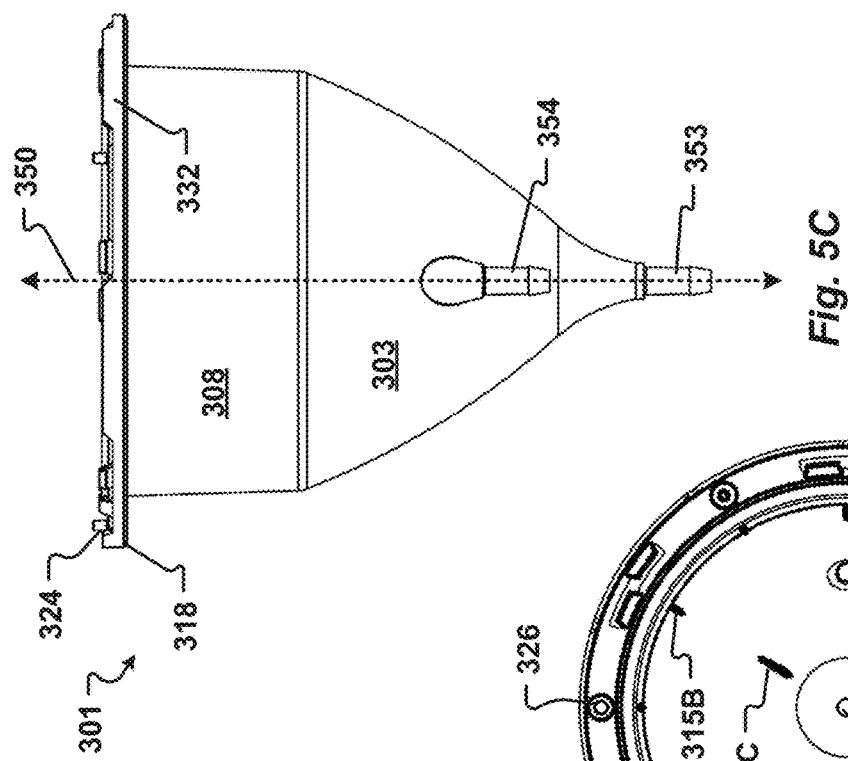
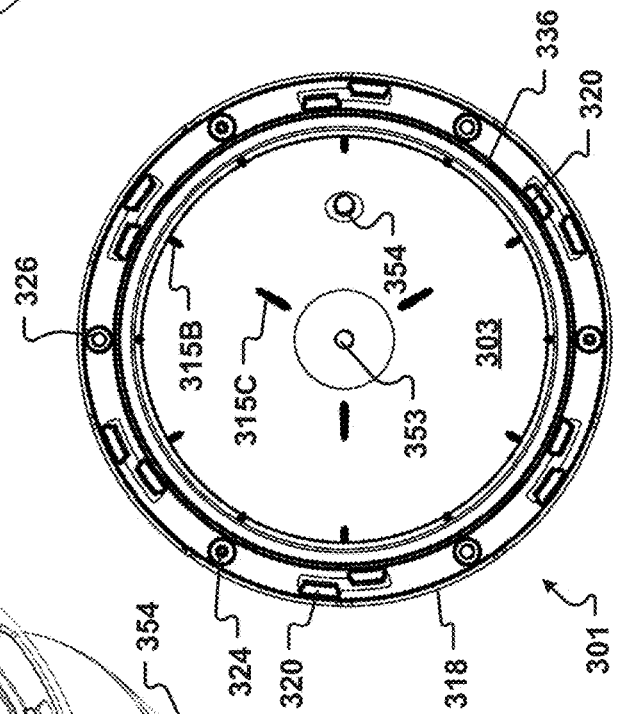
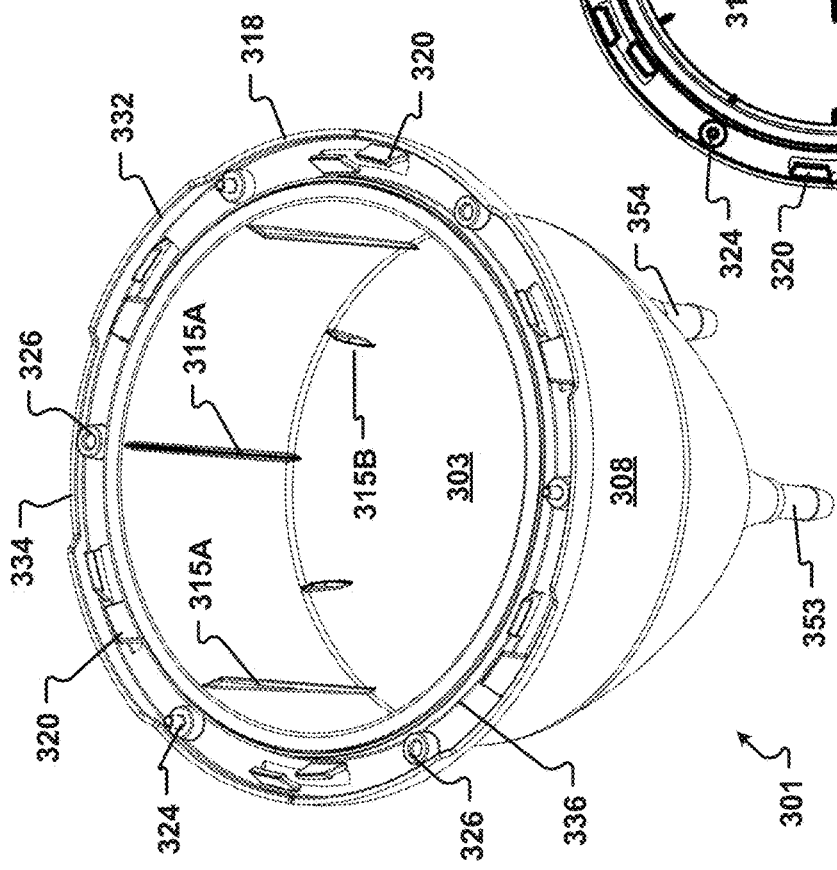
Fig. 5A
Fig. 5B
Fig. 5C

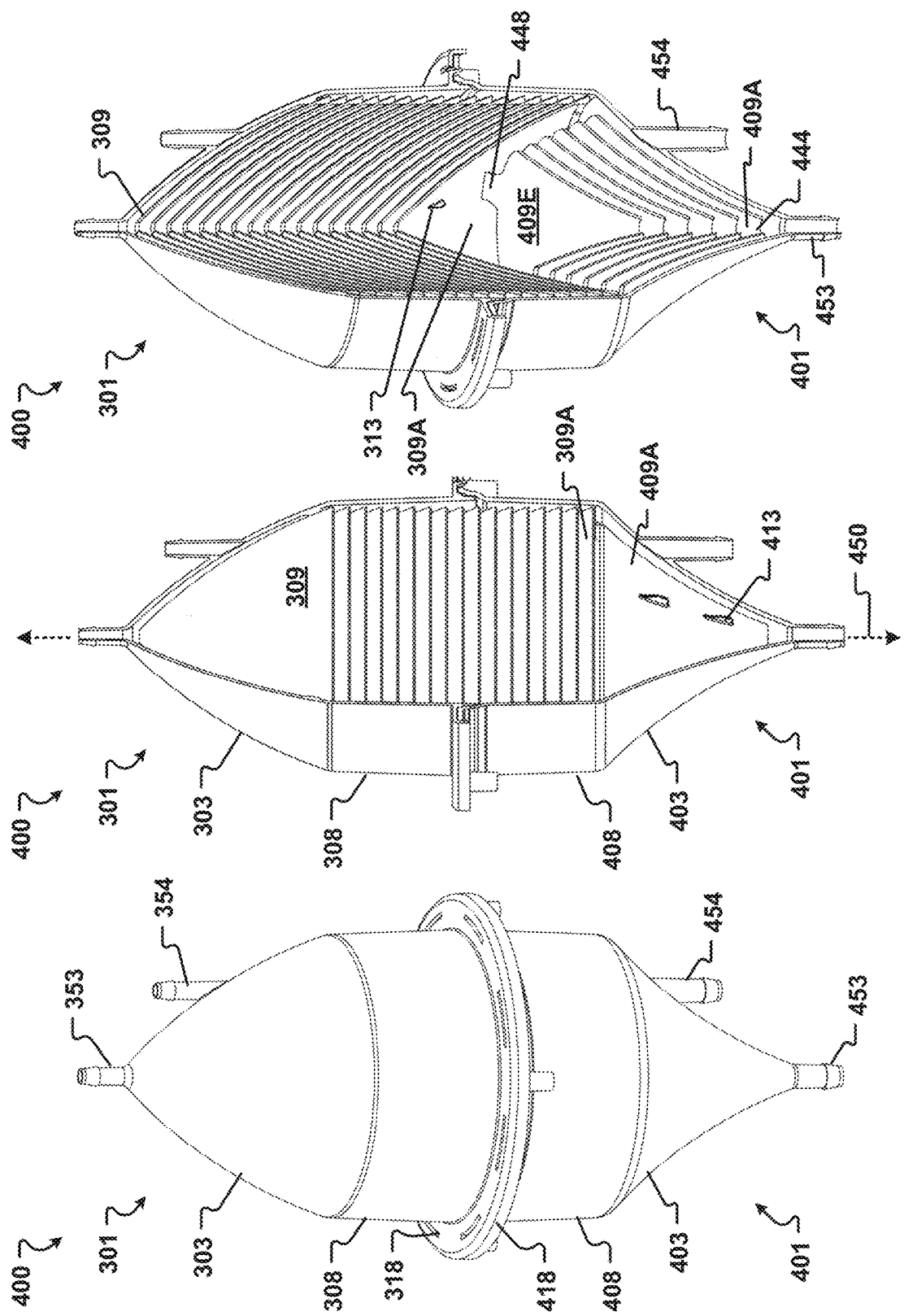

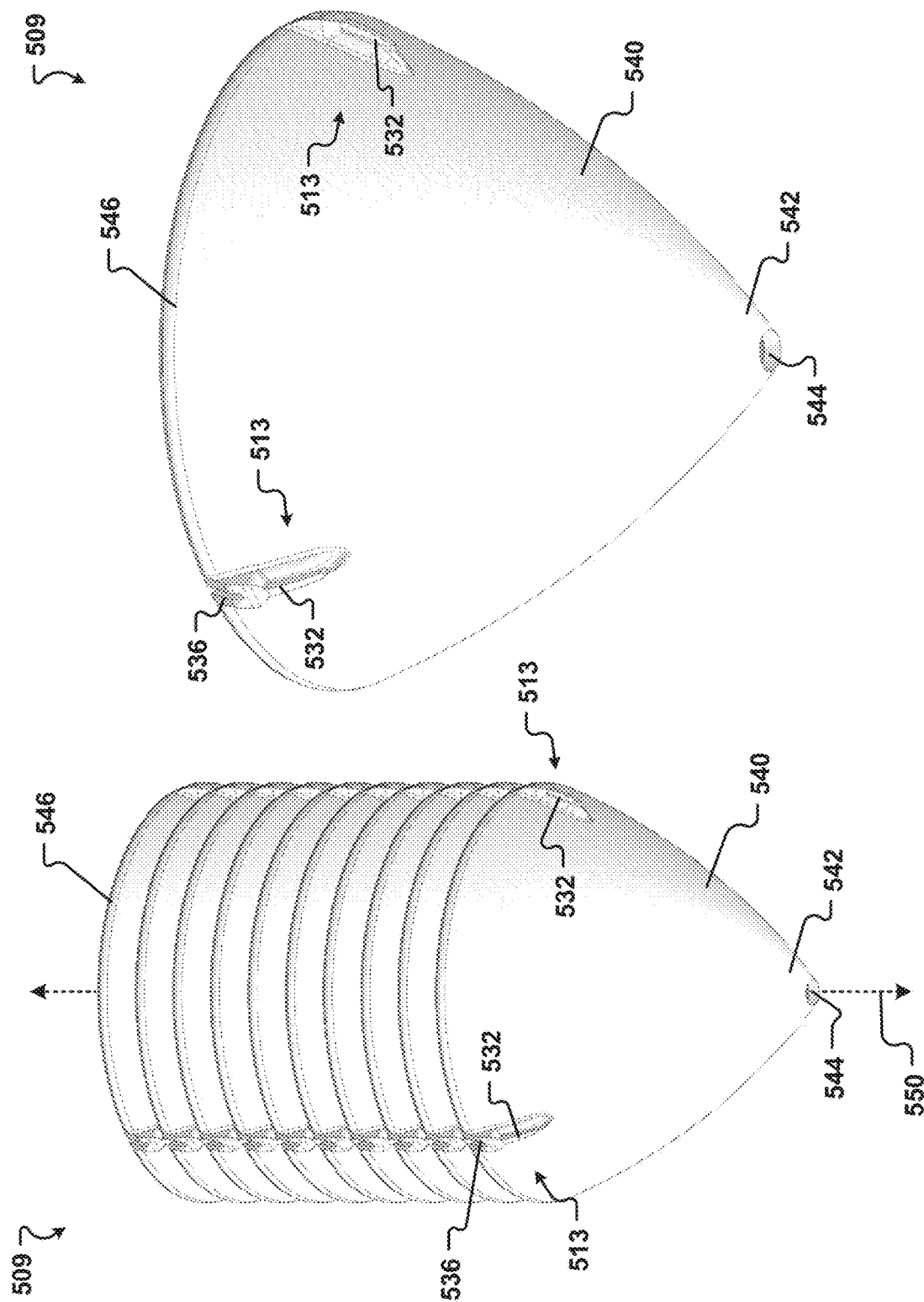

PARTICLE SETTLING DEVICES

CROSS REFERENCE TO RELATED APPLICATION

This application claims the benefit of priority under 35 U.S.C. § 119(e) to U.S. Provisional Patent Application Ser. No. 62/659,295 filed Apr. 18, 2018 and is related to U.S. patent application Ser. No. 15/586,902, filed May 4, 2017, which application is a continuation in part of U.S. patent application Ser. No. 15/324,062, filed Jan. 5, 2017, and to PCT Application No. PCT/US2015/063195 having an international filing date of Dec. 1, 2015 and which designated the United States. This application is also related to U.S. Provisional Patent Application No. 62/332,546, filed May 6, 2016, and to U.S. Provisional Patent Application No. 62/459,509, filed Feb. 15, 2017. U.S. patent application Ser. No. 15/324,062 is a national stage application under 35 U.S.C. 371 of PCT Application No. PCT/US2015/039723 having an international filing date of Jul. 9, 2015, which designated the United States, which PCT application claims the benefit of U.S. Provisional Patent Application No. 62/022,276, filed Jul. 9, 2014, and to U.S. Provisional Patent Application No. 62/037,513, filed Aug. 14, 2014. PCT Application No. PCT/US2015/063195 claims the benefit of U.S. Provisional Patent Application No. 62/086,122, filed Dec. 1, 2014. All of these applications are incorporated herein by reference in their entirety.

FIELD

This disclosure provides cell or particle settling devices with enhanced settling on multilayered inclined surfaces. The devices of the present disclosure have applications in numerous fields, including: (i) high cell density biological (mammalian, microbial, plant or algal) cell cultures secreting polypeptides, hormones, proteins or glycoproteins, vaccines or vaccine-like particles, or other small chemical products, such as ethanol, isobutanol, isoprenoids, flavor and fragrance compounds, etc.; (ii) separating and recycling porous or non-porous solid catalyst particles catalyzing chemical reactions in liquid or gas phase surrounding solid particles; (iii) separating and collecting newly formed solids in physical transformations such as crystallization, flocculation, agglomeration, precipitation, etc., from the surround liquid phase; (iv) capture and purification of secreted proteins, such as monoclonal antibodies, and others, on affinity ligands, such as protein A immobilized on microspherical beads; (v) in vitro expansion of various mammalian cells, such as human mesenchymal stem cells, differentiated human cells (e.g. cardiomyocytes or red blood cells), modified human cells (e.g. chimeric antigen receptor transfected T lymphocytes or CAR-T cells, etc. for autologous or allogenic cell therapy applications); and (vi) clarifying process water in large scale municipal or commercial waste water treatment plants by settling and removing complex biological consortia or activated sludge or other solid particles.

DESCRIPTION OF RELATED ART

Of all the above-mentioned fields of application for settling devices, the more immediately applicable well-established field is the production of biological proteins, polypeptides or hormones secreted from suspension cultures of recombinant microbial or mammalian cells. Most common methods of producing biological proteins in recombinant mammalian and microbial cells rely on fed-batch cultures, wherein cells are grown to high cell densities and then typically exposed to an induction medium or inducer to trigger the production of proteins. If the desired proteins are secreted out of the cells, it is more profitable to switch from a fed-batch culture to a continuous perfusion culture, which can maintain high cell density and high productivity over a much longer duration of culture. During continuous perfusion cultures, live and productive cells are retained or recycled back to the bioreactor while the secreted proteins are continuously harvested from the bioreactor for downstream purification processes.

Some key advantages of continuous perfusion cultures over fed-batch cultures are: (1) the secreted protein products are continuously removed from the bioreactor, without subjecting these products to potential degradation by proteolytic and/or glycolytic enzymes released into the culture medium from dead cells; (2) live and productive cells are retained or recycled back to achieve high cell densities in continuous perfusion bioreactors, where they continue to produce valuable proteins inside the controlled bioreactor environment for much longer culture duration, rather than being killed and removed from the bioreactor at the end of each fed-batch culture; (3) the perfusion bioreactor environment can be maintained much closer to steady state conditions (thereby maintaining a more consistent product quality by design) with the continuous addition of fresh nutrient media and removal of waste products along with the harvested protein products, unlike the dynamically changing concentrations of nutrients and waste products in fed-batch culture; and (4) with a subset of cell retention devices, smaller dead or dying cells can be selectively removed from the perfusion bioreactor before these cells lyse and release their intracellular enzymes, thereby maintaining a high viability fraction of cells and high quality of the secreted protein products as they are harvested.

Many cell retention devices have been developed in the mammalian cell culture industry, such as the internal spin filter devices (Himmelfarb et al., Science 164: 555-557, 1969), external filtration modules (Brennan et al., Biotechnol. Techniques, 1 (3): 169-174, 1987), hollow fiber modules (Knazek et al., Science, 178: 65-67, 1972), gravitational settling in a cyclone (Kitano et al., Appli. Microbiol. Biotechnol. 24, 282-286, 1986), inclined settlers (Batt et al., Biotechnology Progress, 6:458-464, 1990), continuous centrifugation (Johnson et al., Biotechnology Progress, 12, 855-864, 1999), and acoustic filtering (Gorenflo et al., Biotechnology Progress, 19, 30-36, 2003). The cyclones were found to be incapable of producing enough centrifugal force for sufficient cell separation at the device sizes and harvest flow rates used in the mammalian cell culture experiments (Kitano et al., 1986) and mammalian cells are seriously damaged at higher flow rates (and centrifugal forces) necessary for efficient cell separation (Elsayed, et al., Eng. Life Sci., 6: 347-354, 2006). While most of the other devices adequately retain all mammalian cells from the harvest, these devices are unable to separate dead cells from the live cells desired in the bioreactor. Consequently, dead cells keep accumulating inside the perfusion bioreactor and the membrane filters get clogged, necessitating the termination of the continuous perfusion bioreactor, typically within three or four weeks of mammalian cell culture.

Among all the cell retention devices available today, only the inclined settlers (Batt et al., 1990, supra and Searles et al., Biotechnology Progress, 10:198-206, 1994) enable selective removal of smaller dead cells and cell debris in the overflow or harvest stream, while bigger, live and productive mammalian cells are continually recycled via the underflow back to the perfusion bioreactor. Therefore, it is feasible to continue the perfusion bioreactor operation indefinitely at high viability and high cell densities while the protein product is continuously harvested from the top of the inclined settler.

The inclined settler has previously been scaled up as multi-plate or lamellar settlers (Probstein, R. F., U.S. Pat. No. 4,151,084, April 1979) and used extensively in several large-scale industrial processes such as wastewater treatment, potable water clarification, metal finishing, mining and catalyst recycling (e.g. Odueyngbo et al., U.S. Pat. No. 7,078,439, July 2006).

Citing our first demonstration of a single plate inclined settler (Batt et al., 1990) to enhance productivity of secreted proteins in mammalian cell culture applications, a multi-plate or lamellar settler device has been patented for the scale up of inclined settlers for use in hybridoma cell culture (Thompson and Wilson, U.S. Pat. No. 5,817,505, October 1998). Such lamellar inclined settler devices have been used to culture recombinant mammalian cells in continuous perfusion bioreactors at high bioreactor productivity (due to high cell density) and high viability (>90%) for long durations (e.g. several months without any need to terminate the perfusion culture). U.S. Patent Publication No. 2011/0097800 to Kauling et al., describes a scaled-up version of inclined settlers that uses cylindrical tubes wrapped at inclined angles. The device is described as useful in the culturing of larger mammalian cells, such as CHO, BHK, HEK, HKB, hybridoma cells, ciliates, and insect cells.

None of these cell retention devices have been demonstrated for harvesting secreted protein products in perfusion bioreactor cultures of the smaller, and hence more challenging, microbial cells. Lamellar settlers have been tested with yeast cells to investigate cell settling with limited success (Bungay and Millspaugh, Biotechnology and Bioengineering, 23:640-641, 1984). Hydrocyclones have been tested in yeast suspensions, mainly to separate the yeast cells from beer, again with only limited success (Yuan et al., Bioseparation, 6:159-163, 1996; Cilliers and Harrison, Chemical Engineering Journal, 65:21-26, 1997).

A modified cyclone with a spiral vertical plate inside the cyclone was proposed to improve the separation efficiency in wastewater treatment (Boldyrev VV, Davydov EI, settling tanks, as described in Russian Patent No. 2,182,508) and an earlier description of this arrangement has been described for the decantation of solids in liquid suspension (U.S. Pat. No. 4,048,069, September 1977). The modified cyclone disclosed in Russian patent No. 2,182,508 includes a spiral wound plate housed in a vertical cylindrical barrel with a conical bottom. A slit is provided along the entire height of a central waste water inlet tube, which is plugged at the bottom in order to channel waste water from the inlet tube into the vertical spiral wound plate. The spiral starts at the central tube and ends at the wall of the cylindrical housing, forming a channel through which particle-laden waste water flows. The particles settle in the vertical sedimentation column of the spiral channel. The height of the settler zone is the vertical height of the spiral plate and the width of the channel is formed by the walls of the spiral wound plate, which is held constant throughout its length. A pipe for removing the purified water is installed at the upper part of the cylindrical body. A conduit for removing sediment is installed at the bottom of the conical bottom portion. In operation, waste water enters through the central tube and enters the spiral zone through the slit or opening. The spiral channel serves to increase the flow path and hence increase the residence time of liquid in the settler. The spiral also serves to increase the contact (wall) area for the fluid. The main driving force in clarification is gravity acting on the particles of the suspension, as the suspension goes around the spiral-wound vertical sedimentation column. The slurry that is left on the wall of the spiral or in the channel, falls into the conical bottom of the settler, and is removed periodically from the settler. Purified water is drawn from a pipe on the side of cylindrical housing near the top.

As described in the Russian patent document, the flow pattern of the waste water-containing solids is reversed from the typical flow pattern of a common cyclone, as the dirty water enters at the center, via the central tube and enters into the spiral channel through the slits, and the purified water is removed from the periphery or outside of the vertical cylindrical body via a purified water pipe. This modified and flow-reversed cyclone device has not been proposed for, or applied to, any fields other than waste water treatment.

Thus, a particle settling device that can leverage centrifugal forces and gravitational forces on particles in liquid suspension in a relatively small space is desired.

SUMMARY

This disclosure provides cell or particle settling devices with enhanced settling on multilayered, inclined surfaces arranged within a housing. The housing may be a cyclone housing. The particle separation devices of this disclosure may be used in numerous applications and represent a large improvement over the prior art separation devices. In these settling devices, the inclined surfaces may be attached to a plurality of vertical cylindrical plates. The settling devices may include a spiral conical surface, or several inclined plates approximating an angled conical surface connected to the bottom of a spiral. The numerous, layered inclined plates enhance the settling efficiency of the particles from the bulk fluid moving either downward or upward inside a conical assembly in which the liquid volume moves progressively from the periphery of the conical or spiraled settling surfaces to the center of the settler device.

The settler devices of this disclosure may include a housing that encloses a series of stacked cones positioned inside the housing, tapering down to a central opening, with no vertical plates. The cones of this embodiment are supported in the stack, one above the other, by supports that maintain a distance (or channel width) between the successive cones in the stack. The supports may comprise three or more projections attached to the upper and/or lower surface of one or more of the cones to position successive cones at a desired distance (the desired channel width) apart. Optionally, the supports may comprise at least three L-shaped elements interconnected to a surface of each cone that is distal to the truncated apex of the cone. The L-shaped elements include a first side interconnected to a second side at an apex and are interconnected to the surface such that the first side supports a second cone in the stack of cones. The second side is substantially parallel to the surface of the cone. Optionally, the second side may project beyond the cone to space the cone from an interior surface of the housing. In some embodiments there is no plug or other impediment preventing the flow of liquid or suspended particles from the stacked conical surfaces toward the central opening.

The settler devices of this disclosure may include a housing enclosing:

1) a first stack of two or more stacked cones, each having a central opening, and, 2) an optional second stack of two or more stacked cones, each having a central opening, joined at or near their bottom with conical surfaces tapering down to a central opening at the bottom of the housing.

The stacked cones (in both the first and optional second stack of two or more stacked cones) comprise at least three projections supporting each cone above the next successive cone in the stack. The projections are preferably placed at a substantially constant distance and are formed at a generally equal size to hold each successive cone in the stack at about an equal spacing between all of the cones in the stacks. In one embodiment, there are at least three projections for each cone to properly support each successive cone, but each cone may comprise more than three projections, as needed to adequately or properly support the cone. For example, each cone may comprise four projections, or may comprise eight projections, to support the next successive cone in the stack.

The projections, or "vertical supports," may represent an impediment to settled particles or cells sliding down the surface of a cone towards the central opening or the gap around the inner circumference of the housing between the housing and the cones. These projections are attached to one surface of a cone, but these projections need not attach to another cone in a stack of cones. Thus, these projections need not, and in most embodiments do not, attach two or more cones in a stack to one another.

There is preferably a substantially constant spacing between each successive conical surface created by the projections supporting each successive cone in a stack of cones. The spacing between successive cones may be varied between about 1 mm to about 2.5 cm.

This arrangement of settling surfaces, provided by the successive stacks of cones, each of which is supported by the next successive cone, but is not permanently attached to the next successive cone, is particularly useful for separation applications in which the particle settling device, and the conical surfaces therein, requires regular or continual service, such as disassembly and cleaning of the conical settling surfaces within the settler device.

This arrangement of first and optional second stacks of cones significantly enhances the settling efficiency of particles from a bulk fluid as the bulk fluid moves through the settling device. As the bulk liquid, including particles such as cells, moves through the stacked cones of the settler device of this disclosure, bigger particles (e.g., live and productive cells) settle on the surface of the cones. Cells sliding down the upper or first stack of cones, slide down the conical surfaces to the outer edges of the cones and fall down vertically into the conical section of the housing. Additionally, cells sliding down the lower or second stack of cones, slide down the conical surfaces to the central opening of the cones and fall down vertically towards the central opening of the housing.

These devices can be scaled up or down to suit the separation needs of different industries or applications or sizes as the separation surface is scaled up or down volumetrically in three dimensions, compared to the more typical one- or two-dimensional scaling of previous settling devices.

Scale up of the devices of this disclosure can be performed simply by increasing the diameter of the housing (and correspondingly increasing the diameter of cones stacked inside) and/or increasing the height of the housing (which increases the number of cones in either one or both of the first and second stack of cones). The effective projected area for cell settling increases proportional to the square of the diameter of the housing and increases proportional to the height of internal cylinders. The effective settling area of the compact settling devices of this disclosure scales up proportional to the cube of housing diameter (assuming the height of the internal settler is also increased proportionally) or equivalently, to the volume of housing. This three dimensional or volumetric scale-up of the effective settling area makes the settling device of this disclosure much more compact compared to previous inclined settler devices.

The radial spacing in the annular regions between different cylinders or cones can be between about 1 cm to about 10 cm, with an optimum around about 2.5 cm. A small clearance of about 1 mm between the inclined settling cones and the internal surface of the next successive cone provides useful space for settled particles (for example cells) to slide down the surface of the cones and exit the cones on the side, rather than sliding all the way down to the bottom of the cone. The side-exiting cells settle vertically along the inside of each cylinder. When these settling cells reach the conical surface at the bottom of each cylinder, they slide down on the inclined surface on the cone to the central opening at the bottom of the cyclone housing. An advantage of the increasing fluid velocity while going down the inclined conical surface to the central opening is that the increasing number of settled cells sliding down the cone are swept down to the central opening, rather than being allowed to accumulate by the faster liquid velocities.

The angle of inclination for the settling surfaces may or may not be constant, ranging between about 15 degrees to about 75 degrees from the vertical. For use with stickier particles (typically mammalian cells), the angle of inclination may be closer to the vertical (i.e., around 15 degrees from vertical). For use with non-sticky solid catalyst particles, the angle of inclination can be further from vertical (for example, around 75 degrees from vertical). In some embodiments, the conical surfaces have an arcuate longitudinal cross section such that the angle of inclination varies with respect to a longitudinal axis from between about 10 degrees to about 80 degrees, or about 15 degrees to about 75 degrees.

All of the settler devices of this disclosure may include a closure or lid over at least a portion of the housing at an end of the housing opposite the first opening. In all of these embodiments, the closure or lid may also include an outlet or port for removing liquids or entering liquids into the settler device. The opening and the additional ports or outlets in the housing and/or the lid are in liquid communication with the outside and the inside of the housing to allow the passage of liquids into and/or out of the housing of the settler device, and in each instance of such opening or inlet/outlet, these passage ways into and out of the housing may include valves or other mechanisms that can be opened or closed to stop or restrict the flow of liquids into or out of the settler devices of this disclosure.

The particle settling devices of this disclosure may include a housing and at least one vertical tube disposed inside the housing, the at least one vertical tube joined at one end with a conical surface tapering down to a first opening in the cyclone housing. There is at least one additional opening in the housing substantially opposite the first opening.

The angle of inclination for the conical surfaces is about 45 degrees from vertical in one embodiment, or may vary between about 15 degrees from vertical and about 75 degrees from vertical. Optionally, the conical surfaces and/or the top or bottom of the housing, may have a concave or convex shape such that the angle of inclination varies between about 15 degrees from vertical and about 75 degrees from vertical.

The width of an annular ringed channel formed between adjacent vertical tubes is between about 1 mm and about 50 mm. The number of vertical tubes within the settler device may be between about 2 and about 30.

The settler device may include a closure over at least a portion of the housing at an end of the housing opposite the first opening. At least one additional opening in the housing may be configured to open from a side of the housing tangential to at least one vertical tube, in liquid communication with the outside and the inside of the housing.

A liquid harvest outlet may be formed in the closure, in liquid communication with the outside and the inside of the housing.

Another aspect of the present disclosure is a particle settling device that may include, but is not limited to, a housing including one or more of: (1) a first conical portion; (2) a second conical portion; (3) a cylindrical portion located between the first and second conical portions; (4) at least one inlet for introducing a liquid into the housing; (5) a first outlet port; (6) a second outlet port; and (7) a first stack of cones located within the housing. In one embodiment, the first outlet port is associated with the first conical portion and the second outlet port is associated with the second conical portion. Optionally, the liquid introduced into the housing may be a liquid suspension including particles. The particles may be of a plurality of sizes.

In one embodiment, the first outlet port may be for harvesting a clarified liquid. The clarified liquid may include a first subset of particles. The first subset of particles may comprise cell debris, dead cells, and the like. Optionally, the first outlet port may be formed in a closure of the housing. The first outlet port being in liquid communication with the outside and the inside of the housing.

Optionally, in another embodiment, the second outlet port may be for harvesting a concentrated liquid. The concentrated liquid may include a second subset of particles, such as live cells. Typically, particles of the second subset of particles are generally larger than particles of the first subset of particles. Each particle of the second subset of particles generally has a greater mass than the particles of the first subset of particles. The second outlet port is in liquid communication with the outside and the inside of the housing.

The first stack of cones occupies at least a portion of the first conical portion. Optionally, the first stack of cones occupies at least a portion of the cylindrical portion. Optionally, one or more cones of the first stack of cones includes a truncated apex oriented towards the first outlet port. Additionally, or alternatively, at least one cone of the first stack of cones is devoid of the central opening. In another embodiment, each cone of the first stack of cones includes an open base oriented towards the second outlet port. The cones of the first stack of cones are generally centered in the housing, for example, the cones of the first stack of cones may be centered around a substantially central opening formed by the truncated apex of one or more of the cones.

Optionally, the housing may further include a second stack of cones. The second stack of cones may occupy at least a portion of the second conical portion, and may occupy at least a portion of the cylindrical portion. In one embodiment, each cone of the second stack of cones is transverse to the cones of the first stack of cones.

Optionally, an angle of inclination for a surface of a cone in the first stack of cones may vary between about 15 degrees to about 75 degrees from vertical. In one embodiment, the surface of a cone is convex or concave such that a cross-section of the cone surface defines an arcuate line. In another embodiment, the angle of inclination of the cones may be constant at any angle between 15 and 75 degrees from vertical. In one embodiment, the angle of inclination of the cones is about 45 degrees.

In another embodiment, each cone of the second stack of cones includes a truncated apex oriented towards the second outlet port. Each cone of the second stack of cones may also include an open base oriented towards the first outlet port. In one embodiment, the cones of the second stack of cones are generally centered in the housing. In another embodiment, the cones of the second stack of cones are about centered around a substantially central opening formed by the truncated apex of one or more of the cones.

In one embodiment, an angle of inclination for a surface of a cone in the second stack of cones is between about 15 degrees to about 75 degrees from vertical. The angle of inclination of the cones in the second stack of cones may be about 45 degrees.

In one embodiment, the cones of the first stack of cones have a substantially uniform spacing. Additionally, the cones of the second stack of cones may have a substantially uniform spacing. In one embodiment, the cones of the first stack of cones have a different spacing compared to the cones of the second stack of cones.

The at least one inlet is configured as an inlet port in liquid communication with the outside and the inside of the housing. The at least one inlet may be associated with at least one of the first conical portion, the second conical portion, and the cylindrical portion of the housing. In one embodiment, a first inlet of the at least one inlet is associated with the cylindrical portion of the housing. In another embodiment, a second inlet of the at least one inlet is associated with one of the first and second conical portions. In yet another embodiment, the second inlet is associated with the second conical portion. In another embodiment, the at least one inlet is configured to be interconnected to a disposable bioreactor bag. The disposable bioreactor bag may comprise a plastic material.

A configuration of the particle settling devices of this disclosure may include a housing, comprising: (a) a first conical portion; (b) a second conical portion; (c) a cylindrical portion located between the first and second conical portions; (d) at least one inlet for the liquid suspension to enter the housing; (e) the first outlet port for harvesting the clarified liquid; (f) the second outlet port for discharging the concentrated liquid suspension; and (g) a first stack of cones located within the housing. In this device, the first stack of cones may occupy at least part of the first conical portion, and may occupy at least part of the cylindrical portion. Each cone of the first stack of cones includes (i) a truncated apex positioned distal to the second conical portion, and (ii) an open base positioned proximate to the second conical portion. Optionally, the cones of the first stack are generally centered around a substantially central opening formed by the truncated apex in each cone in the first stack of cones.

An angle of inclination for a surface of a cone in the first stack of cones may vary between about 15 degrees to about 75 degrees from vertical. For example, a cross section of the cone surface defines an arcuate line. These cones may have a convex or a concave surface. In other embodiments, the angle of inclination of the cones is constant, and may be, for example, about 45 degrees. The cones of the first stack of cones preferably have a substantially uniform spacing.

An angle of inclination for a surface of a cone in the second stack of cones may vary between about 15 degrees to about 75 degrees from vertical. In another embodiment, the angle of inclination of the cones in the second stack of cones is about 45 degrees.

Yet another aspect of the present disclosure is a particle settling device, comprising: (A) a housing; (B) at least two conical plates disposed inside the housing; (C) a first opening in the housing; and (D) a second opening in the housing. In one embodiment, the at least two conical plates are stacked one above the other. Preferably, the housing includes between about 3 and about 30 conical plates. The at least two conical plates may be separated by a substantially constant distance. Optionally, a width of a channel formed between adjacent surfaces of the at least two conical plates is between about 1 mm and about 50 mm. Three or more supports may hold each of the conical plates in the stack.

Each of the conical plates may include a truncated apex proximate to the first opening and an open base positioned distal to the first opening. The conical plates may be generally centered in the housing, and are arranged in a substantially vertical position within the housing. The angle of inclination for a surface of each of the at least two conical plates may vary between about 15 degrees and about 75 degrees from vertical. The conical plates may have a concave shape relative to a longitudinal axis. The conical plates may have a convex shape relative to the longitudinal axis. Accordingly, a cross-section of a conical plate may define an arcuate line. In one embodiment, the conical plates have a shape defined by at least one radius of curvature.

In these devices, the housing includes a cylindrical portion and a conical portion. The first opening may be associated with the conical portion. Optionally, the second opening may be associated with the cylindrical portion. The second opening may be positioned in a sidewall of the cylindrical portion. The second opening may be positioned in a lid associated with an open end of the cylindrical portion. The second opening may be positioned in the conical portion.

Another aspect of the present disclosure is a settling device which includes, but is not limited to: (1) an upper housing including: a first conical portion; a first cylindrical portion; and at least one port; (2) a lower housing interconnectable to the upper housing and including: a second conical portion; a second cylindrical portion; and at least one port; and (3) a stack of cones located within the settling device, each cone of the stack of cones including a small opening oriented towards the first conical portion and a large opening oriented towards the second conical portion, the first stack of cones generally centered around a longitudinal axis of the settling device. Optionally, the upper housing further comprises a first flange configured to engage a second flange of the lower housing. The upper housing may be permanently joined to the lower housing.

In these devices, a surface of a cone of the first stack of cones is at an angle of between approximately 15 degrees to about 85 degrees relative to the longitudinal axis. Optionally, the first and second conical portions are concave inwardly towards the longitudinal axis. In one embodiment, a longitudinal cross-section of a body of a cone forms a line with an arcuate shape.

Additionally, or alternatively, the first conical portion is concave inwardly towards the longitudinal axis and the second conical portion is concave outwardly away from the longitudinal axis. In one embodiment, the settling device includes a second stack of cones located within the settling device. In another embodiment, each cone of the second stack of cones includes a small opening oriented away from the first conical portion and a large opening oriented towards the first conical portion. Optionally, the cones of the second stack of cones have bodies that are concave outwardly away from the longitudinal axis.

In any of the settler devices of this disclosure, the housing and/or the cones and/or any other components of the device may be composed of a metal or a plastic. The plastic may be one or more of polypropylene, polyethylene, polycarbonate, polystyrene, and the like. In one embodiment, the settling device is formed entirely of plastic. In another embodiment, at least one cone of the stack of cones is composed at least partially of stainless steel. The metal surfaces (especially stainless steel) may be electropolished to provide a smooth surface. Similarly, in any of the settler devices of this disclosure, the housing and/or the cones and/or any other components of the device may be completely or partially coated with one or more of a non-sticky plastic, such as Teflon or silicone.

In any of the settler devices of this disclosure, the housing may further include a fluid jacket associated with one or more of the first conical portion, the second conical portion, and/or the cylindrical portion. In one embodiment, the fluid jacket is associated with the second conical portion and the cylindrical portion. The fluid jacket may include at least one port to receive a fluid of a predetermined temperature. Optionally, the fluid jacket may include a second port to extract fluid from the fluid jacket. Water or other fluids may be directed into the fluid jacket to maintain the cyclone housing and all of its contents within a desired temperature range. Ports may be formed in the outer wall of the cyclone housing to reach the jacket. The ports may function as inlet or outlet ports for the circulation of cooling or heating fluids through the jacket.

In any of the settler devices of this disclosure, one or more sensors may be positioned to monitor physical conditions within the interior of the settler device. Additionally, or alternatively, at least one sensor may be positioned to monitor conditions within a tubing line interconnected to the settler devices of this disclosure. The tubing line may be a return line interconnected to a bottom outlet port of the settler device.

These sensors may be selected to determine one or more of pH, dissolved oxygen (DO), glucose, temperature, and $CO_2$ (including dissolved $CO_2$, known as partial $CO_2$) within the housing or the tubing line. The sensors may include one or more probes in contact with a solution within the housing or the tubing line. The probe may be affixed to an interior surface of the settler device or the tubing line. In preferred embodiments, at least one sensor and/or probe is positioned within the lower conical portion of the settler device, and may be spaced from one or more of the side port and the bottom port.

These probe(s) may transmit data without contact to a reader. In this manner, the probe may measure a condition within the settler device and/or the line and transmit data to the reader outside the settler device. One or more of the probes may be a fluorescent probe. One or more of pH, DO, glucose, temperature, and $pCO_2$ may be measured by the probe within the cyclone housing. The probe may be affixed to a portion of the housing. The portion of the housing may be operable to transmit light produced by the fluorescent probe. As described above, a portion of the housing may be transparent or translucent. The reader (or meter) receives light from the fluorescent probe. The reader may also include an optical fiber that collects light transmitted by the fluorescent probe. Suitable probes and readers are available from a variety of vendors, including PreSens Precision Sensing GmbH. In another configuration, the probe within the settler device can transmit data to the reader outside the settler device by a network connection. For example, the probe can communicate with the reader by WiFi, Bluetooth, or any other wireless communication modality.

In operation of a settler device of this disclosure, data from these sensor(s) may be used to adjust a temperature of fluid within the fluid jacket. In another embodiment, the data from the sensor may be used to adjust one or more of pH, temperature, dissolved oxygen concentration, dissolved carbon dioxide, and nutrient concentrations within the particle settling device.

Another aspect of this disclosure provides methods of settling particles or cells in a liquid suspension. The method includes, but is not limited to, (i) introducing a liquid suspension of particles into a particle settling device of this disclosure; (ii) collecting particles from a first opening in a housing of the settler device; and (iii) collecting a liquid from another opening in the settling device. The liquid may be collected from an opening in a closure that covers at least a portion of the housing at an end of the housing opposite the first opening. The liquid may be collected from at least one additional opening in the housing, which opening is configured to open from a side of the housing. In these methods, the step of introducing a liquid suspension into the settler device may include directing a liquid suspension from a plastic bioreactor bag into the particle settling device.

A related aspect of this disclosure provides a method of settling particles in a suspension. The method includes one or more of: (a) introducing a liquid suspension of particles into a settling device which includes: (i) an upper housing with a first conical portion, a first cylindrical portion, and at least one port; (ii) a lower housing interconnectable to the upper housing and including a second conical portion, a second cylindrical portion, and at least one port; and (iii) a stack of cones located within the settling device, each cone of the stack of cones including a small opening oriented towards the first conical portion and having bodies that are concave inwardly toward a longitudinal axis of the settling device; (b) collecting a clarified liquid from the at least one port of the upper housing; and (c) collecting a concentrated liquid suspension from the at least one port of the lower housing.

In these methods, the clarified liquid may include a first subset of particles of the suspension. The first subset of particles may comprise cell debris, dead cells, and the like.

The concentrated liquid may also include a second subset of particles of the suspension, and the second subset of particles may include live cells. The particles of the second subset of particles may be larger than particles of the first subset of particles. Each particle of the second subset of particles may have a greater mass than the particles of the first subset of particles.

In these methods, a second stack of cones may optionally be positioned within the settling device. These cones forming the second stack of cones may have bodies that are concave outwardly away from the longitudinal axis of the settling device.

In any of these methods, the liquid suspension may include at least one of a recombinant cell suspension, an alcoholic fermentation, a precipitating protein solution, a mixture of aqueous fluid containing cells and organic layer containing extracted organic products produced by the cells, a suspension of solid catalyst particles in a liquid mixture containing mostly the products and depleted reactants, a suspension of microspheres coated with protein A molecules which can bind the monoclonal antibodies from the cell culture broth, a suspension of microcarrier beads with mammalian cells growing attached on the beads, a municipal waste water, and an industrial waste water. In these methods, the liquid suspension may include at least one of mammalian cells, bacterial cells, yeast cells, plant cells, algal cells, human stem cells or differentiated human cells, and/or insect cells. In these methods, the liquid suspension may include at least one of biodiesel-producing algae cells, recombinant mammalian and/or murine hybridoma cells, metabolically engineered yeast cells producing secreted organic products, and yeast in beer. In these methods, the liquid suspension may include recombinant microbial cells selected from *Pichia pastoris, Saccharomyces cerevisiae, Kluyveromyces lactis, Aspergillus niger, Escherichia coli,* and *Bacillus subtilis.*

In these methods, the liquid collected from the settler device may include at least one of biological molecules, organic or inorganic compounds, chemical reactants, and chemical reaction products. In these methods, the liquid collected from the settler device includes at least one of hydrocarbons, polypeptides, proteins, alcohols, fatty acids, hormones, carbohydrates, antibodies, antibodies, terpenes, isoprenoids, biodiesel, polyprenoids, and beer. In these methods, the liquid collected from the settler device includes at least one of biodiesel components, secreted therapeutic proteins or hormones such as insulin or its analogs, antibodies, monoclonal antibodies, growth factors, sub-unit vaccines, viruses, virus-like particles, colony stimulating factors, erythropoietin (EPO), secreted flavor or fragrance compounds, including geraniol, myrcene, sweetener protein brazzein, etc.

In these methods, the settler devices of this disclosure can function as a stand-alone perfusion bioreactor for the in vitro expansion of mammalian cells, such as stem cells and CAR-T cells for autologous cell therapy. In these examples of settler devices of this disclosure, inlet of serum-free or animal protein-free cell culture medium may be pumped continuously into the settler/perfusion bioreactor, through bottom port and/or side port. A controlled mixture of $O_2$, $CO_2$, and $N_2$ may also be pumped in to control the pH and DO of the culture supernatant inside the settler/bioreactor. At the end of in vitro cell expansion, the concentrated settled cells collecting at the bottom may be harvested from a bottom port.

The preceding is a simplified summary of the disclosure intended to provide an understanding of some aspects of the settler devices of this disclosure. This Summary is neither an extensive nor exhaustive overview of the invention and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below. As will be appreciated, other embodiments are possible using, alone or in combination, one or more of the features set forth above or described herein. For example, it is contemplated that various features and devices shown and/or described with respect to one embodiment may be combined with or substituted for features or devices of other embodiments regardless of whether or not such a combination or substitution is specifically shown or described herein. Additional aspects of the present invention will become more readily apparent from the Detailed Description, particularly when taken together with the drawings.

BRIEF DESCRIPTION OF FIGURES

FIG. 1 is a front perspective view of a settler device of another configuration of this disclosure;

FIG. 2 is a partial sectional front perspective view of the settler device of FIG. 1 illustrating a stack of convex cones within the settler device;

FIG. 3 is another partial sectional front perspective view of the settler device of FIG. 2;

FIG. 5A is a perspective view of a housing of the settler device of FIG. 1;

FIG. 5B is a top plan view of the housing of FIG. 5A;

FIG. 5C is a side elevation view of the housing of FIG. 5A;

FIG. 10 is a front perspective view of a settler device of yet another configuration of this disclosure;

FIG. 11 is a partial sectional front elevation view of the settler device of FIG. 10

FIG. 12 is another partial sectional front perspective view of the settler device of FIG. 10, illustrating an upper stack of cones and a lower stack of cones within the settler device;

FIGS. 19A and 19B are perspective views of cones of one embodiment of the present disclosure configured for use with the settler device of FIG. 16;

DETAILED DESCRIPTION

Figure 4:
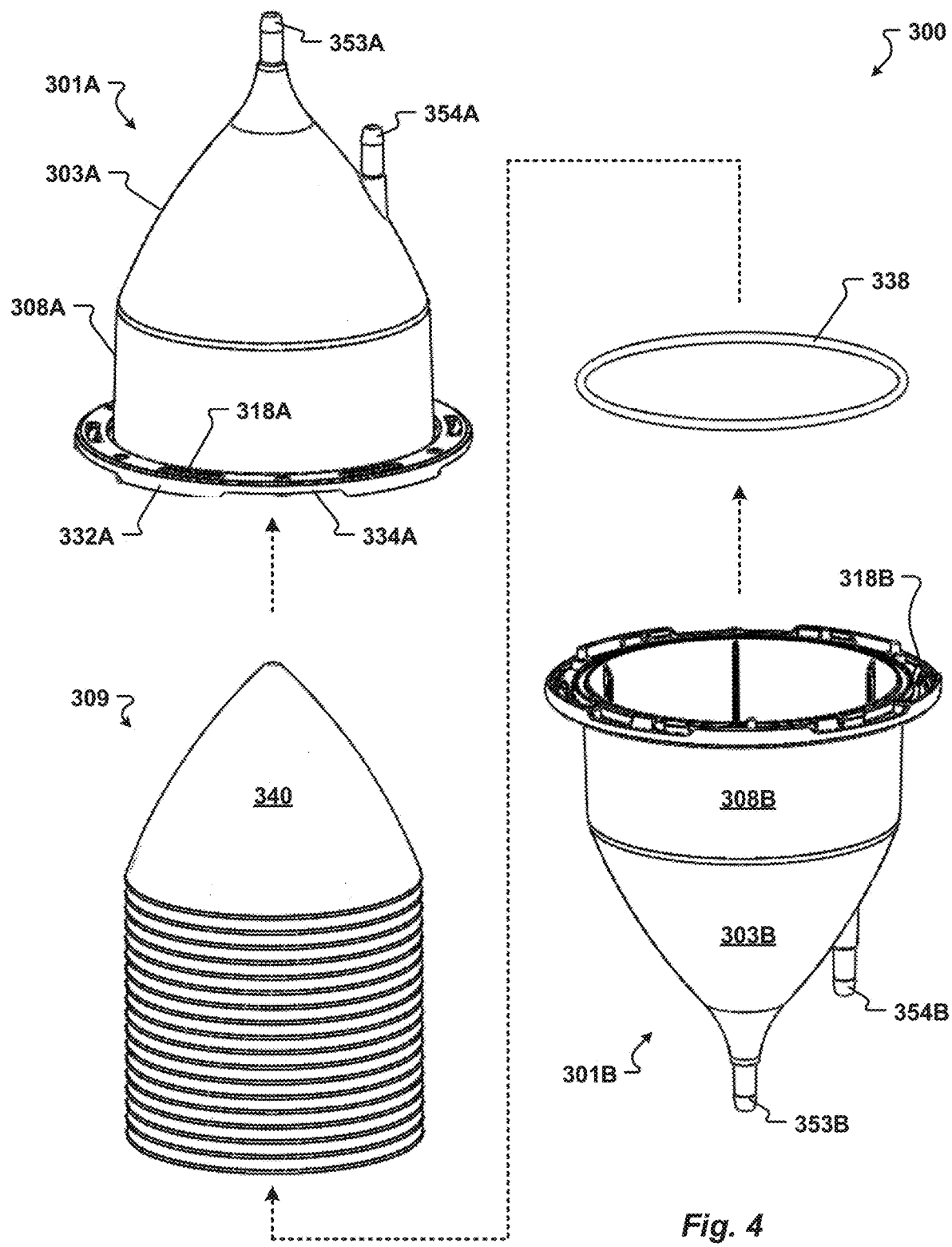
FIG. 4 is an exploded front perspective view of the settler device of FIG. 1.
Figure 6:
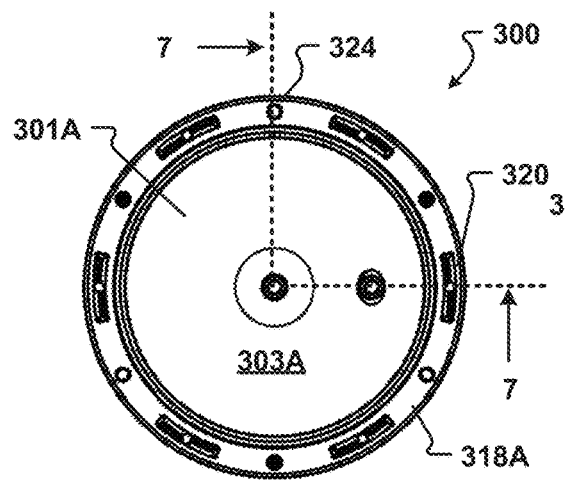
FIG. 6 is a top plan view of the settler device of FIG. 1.

The term "a" or "an" entity refers to one or more of that entity. As such, the terms "a" (or "an"), "one or more" and "at least one" can be used interchangeably herein. The terms "comprising", "including", and "having" can be used interchangeably.

The phrases "at least one," "one or more," and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the disclosure such as impurities ordinarily associated therewith.

The transitional phrase "consisting essentially of" limits the scope of a claim to the specified materials or steps and those that do not materially affect the basic and novel characteristic(s) of the claimed invention.

Referring now to FIG. 1, a configuration of a settler device 300 of the present disclosure, useful for settling particles or cells, is illustrated. The settler device 300 generally includes an upper housing 301A and a lower housing 301B. In one embodiment, the upper and lower housings 301A, 301B are substantially identical. Accordingly, in one embodiment, the housings 301A, 301B are generally interchangeable.

Referring now to FIGS. 2-9, the housings 301A, 301B generally include a conical portion 303A, 303B, a cylindrical portion 308A, 308B, a first port 353A, 353B, and a second port 354A, 354B.

Optionally, the first port 353 is generally aligned concentrically with a longitudinal axis of the housing 301. The first port 353 can be used as an inlet as well as an outlet. In exemplary embodiments, the second port 354 extends through the conical portion 303. The second port 354 can also be used to introduce or remove liquids, gases, and solids from the settler device 300. Optionally, the second port 354 can be aligned generally parallel to the longitudinal axis 350 of the cell settler device. In exemplary embodiments, the second port 354 may extend through the cylindrical portion 308. Other configurations of the first and second ports 353, 354 are contemplated. The housing 301 may also have more than two ports. The ports 353, 354 are configured to interconnect to a tubing line.

Such tubing line may be interconnected to any of the compact cell settler devices of the present disclosure. The line may have a diameter or otherwise be configured to interconnect to any port of embodiments of the present disclosure. The line may optionally include at least one sensor positioned within a hollow interior. The sensors may be in contact with fluid and/or particles within the line. Optionally, the sensors may be arranged on an interior surface of the line, although other configurations are contemplated. The sensors may be operable to monitor one or more of pH, DO, glucose, temperature, and $CO_2$ (including dissolved or partial $CO_2$) in the line. Optionally, one or more of the sensors may comprise a fluorescent probe which emits light that varies based on a condition sensed by the probe. The light may be collected by a reader or meter. Optionally, the light may be collected by an optional fiber cable and transmitted to the meter. The meter is operable to report or display levels of at least one of pH, DO, glucose, temperature, and $CO_2$ sensed by the fluorescent probes. The tubing line may comprise a material that is transparent or at least translucent. Thus, light generated by a sensor may pass through the line. Alternatively, at least a portion of a line is transparent or translucent, similar to a window. Accordingly, light generated by a sensor may be transmitted through window portion and collected by the meter.

Cones 309 can be positioned within the settler device 300. As illustrated in FIGS. 2 and 3, the cones 309 may be arranged in a stack with an open apex 342 oriented toward the first port 353A of the upper housing 301A and a base or large opening 346 oriented towards the first port 353A of the lower housing 301B. In exemplary embodiments, between three and twenty-five cones 309 are arranged in a stack within the settler device 300. However, the housings 301 can be sized to receive any number of cones 309 when the settler device 300 is assembled as illustrated in FIG. 4.

Elements of the settler device 300, such as the housings 301 and the cones 309, can be fabricated of a single-use, disposable plastic. Alternatively, one or more of the housings 301 and the cones 309 can be manufactured of a metal, such as a stainless-steel alloy, or glass. Surfaces of the cones 309, and interior surfaces of the housings 301, may be completely or partially coated with one or more of a non-sticky plastic, teflon, silicone and similar materials known to those of skill in the art. Additionally, or alternatively, the surfaces (especially when formed of stainless steel) may be electropolished to provide a smooth surface. These settler devices can be easily scaled to any desired size.

The housings 301 may optionally include a fluid jacket (not illustrated). The fluid jacket can operate such that water or other fluids may be directed into the fluid jacket through one or more ports to maintain the housings 301 and contents within the settler device 300 within a desired temperature range.

Referring now to FIGS. 5A-5C, a plurality of spacers 315 may project inwardly from an interior surface of the housings 301. The spacers 315 are configured to prevent the stack of cones 309 residing within the settler device 300 from resting against the interior surface of the housings 301A, 301B. Optionally, the spacers 315 can be approximately parallel to the longitudinal axis 350 of the settler device 300. Other configurations of the spacers 315 are contemplated. The spacers 315 have a substantially thin cross-section to prevent or minimize interference with the movement or flow of liquid and suspended particles within the settler device 300.

Figure 7:
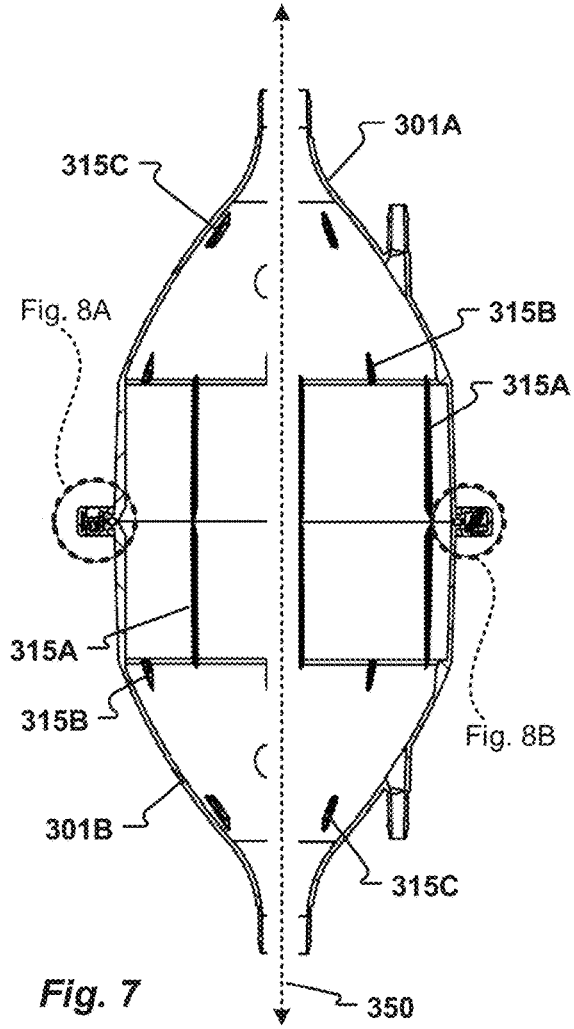
FIG. 7 is a cross-sectional front elevation view of the settler device taken along line 7-7 of FIG. 6 with the stack of cones removed for clarity.

Referring now to FIG. 7, the spacers 315 may include a plurality of first spacers 315A, second spacers 315B, and third spacers 315C. As generally illustrated, in one embodiment, each of the first spacers 315A extends along at least a portion of an interior surface of the cylindrical portion 308. The second spacers 315B extend from an interior surface of the conical portion 303 proximate to the cylindrical portion 308. The third spacers 315C can be separated from the second spacers 315B. Specifically, in one embodiment, the third spacers 315C are arranged closer to the first port 353 than to the cylindrical portion 303.

In one embodiment, the upper housing 301A and the lower housing 301B are fixedly joined. For example, the upper and lower housings 301 can be glued, heat welded, or sonically welded together.

Alternatively, and referring again to FIG. 1, optionally a flange 318 can extend from the generally cylindrical portion 308 of the housings 301. In exemplary embodiments, the flange extends approximately perpendicular to the longitudinal axis 350. The optional flange 318A is configured to interconnect the upper housing 301A to a flange 318B of the lower housing 301B. The flanges 318A, 318B can optionally include projections 320 which are best seen in FIG. 5A. In exemplary embodiments, a catch or hook 322 is formed at a free end of each projection 320.

At least one protrusion 324 can also be formed on the flange 318. The protrusion 324 may have a shape that is generally cylindrical. The protrusion 324 is adapted to be received in a corresponding recess 326 of another flange. Additionally, or alternatively, the flange 318 can include features 332, 334 adapted to align the upper and lower housings 301A, 301B. In exemplary embodiments, the features comprise tabs 332 and associated depressions 334. As illustrated in FIG. 1, when the upper and lower housing 301A, 301B are aligned, the tabs 332 fit into the depressions 334 of an opposing flange.

Figure 8A:
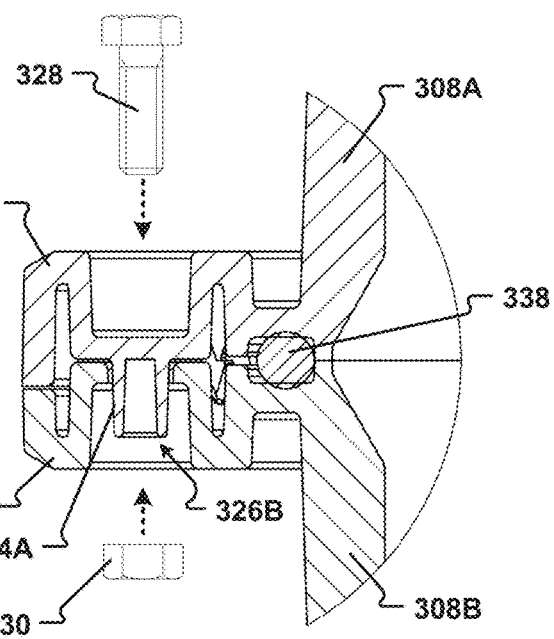
FIG. 8A is a detailed cross-sectional front elevation view of a portion of FIG. 7.
Figure 8B:
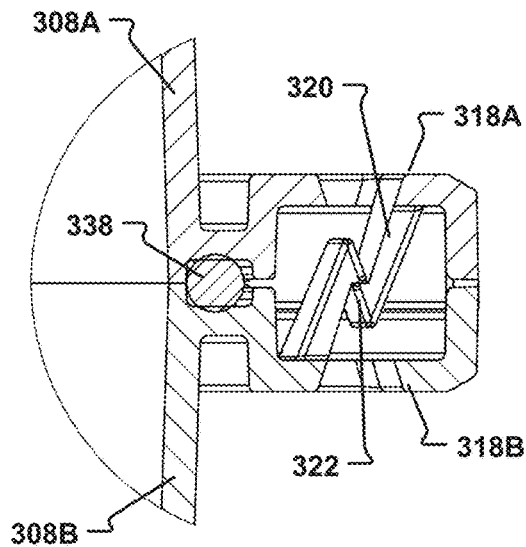
FIG. 8B is another detailed cross-sectional front elevation view of a portion of FIG. 7.

Optionally, the flange protrusion 324 and recess 326 may include bores. The bores of the protrusion and recess are configured to align when a protrusion 324 of an upper housing 301A is received in a recess 326 of a lower housing 301B (as illustrated in FIG. 8A). In this manner, a fixture 328, such as a bolt, can pass through the aligned bores. A nut 330 can then be interconnected to the fixture 328 to releasably lock the housings 301A, 301B together. As generally illustrated in FIG. 8B, the projections 320 of the flange 318 are configured to interlock when an upper housing 301A is aligned with a lower housing 301B. Specifically, in one embodiment, the hooks 322 of the projections 320 releasably interlock.

A groove 336 can be formed in the optional flange 318. The groove 336 is configured to retain a washer or a gasket 338 positioned between the upper and lower housings 301A, 301B as generally illustrated in FIGS. 8A and 8B.

In one embodiment, the conical portion 303 of the housings 301 is not linear. More specifically, the conical portion 303 tapers along an arcuate path from a maximum diameter proximate to the cylindrical portion 308 to a minimum diameter proximate to the first port 353. More specifically, and referring now to FIGS. 5C and 7, a longitudinal cross-section of the conical portion 303 of the housing 301 defines a line with an arcuate shape between the cylindrical portion 308 and the first port 353. In one embodiment, the conical portion 303 is concave inwardly towards a center of the settler device 300. In another embodiment, the conical portion 303 can have a constant radius of curvature. Optionally, in another embodiment, the conical portion 303 can have two or more radii of curvature. For example, the conical portion 303 may have a first radius of curvature proximate to the cylindrical portion 308 and a second radius of curvature proximate to the first port 353. Center points of the first and second radii of curvature are positioned within an interior of housing. Optionally, the slope of the conical portion 308 may vary between approximately 15° and approximately 85° relative to the longitudinal axis 350. In one embodiment, the conical portion 303 includes a convex portion proximate to the first port 353. The convex portion has a radius of curvature with a center point which is outside of the housing.

Referring now to FIGS. 9A-9D, the cones 309 generally include a body 340 having an apex 342 with a small opening 344 and a base with a large opening 346. Optionally, each of the cones is separately formed. In exemplary embodiments, the cones are of substantially the same size and shape.

In some embodiments, the body 340 may not be linear between the small and large openings 344, 346. As illustrated in FIG. 9D, a longitudinal cross-section of the body 340 forms a line with an arcuate shape. The arcuate shape of each cone 309 may be approximately the same as the conical portion 303 of the housing 301.

In some embodiments, the body 340 is concave inwardly toward the longitudinal axis 350. Thus, a line drawn from a point at the large opening 346 to a point at the small opening 344 is within an interior of the body.

Optionally, the body 340 has a constant radius of curvature. Alternatively, the body can have two or more radii of curvature. Thus, the body may have a first radius of curvature proximate to the small opening 344 and a second radius of curvature proximate to the large opening 346. Center points of the first and second radii of curvature are positioned within an interior of cone 309. In this manner, a portion of the body 340 proximate to the small opening 344 can have a slope that is different than a slope of the body proximate to the large opening. For example, proximate to the small opening 344, the body may be aligned at an angle of at least approximately 40° relative to the longitudinal axis 350. In contrast, near the large opening 346, the body can be closer to vertical (or closer to longitudinal axis). More specifically, the body may be sloped at an angle of less than approximately 45° relative to the longitudinal axis at a point proximate to the large opening 346. Optionally, the slope of the body 340 may vary between approximately 5° and approximately 85° relative to the longitudinal axis.

Figure 9A:
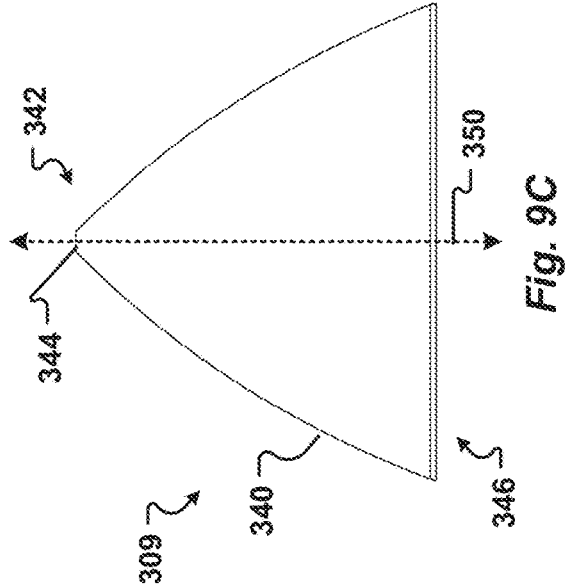
FIG. 9A is a top plan view of a cone of the settler device of FIG. 1.
Figure 9B:
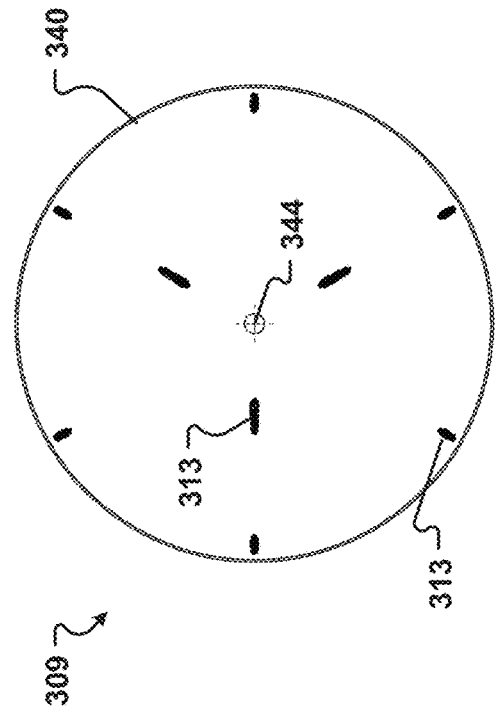
FIG. 9B is a bottom plan view of the cone of the settler device of FIG. 1.
Figure 9C:
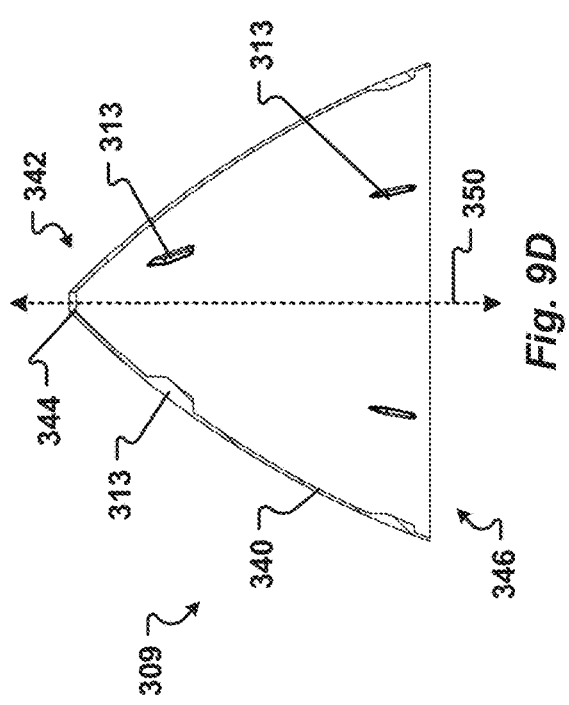
FIG. 9C is a side elevation view of the cone of the settler device of FIG. 1.
Figure 9D:
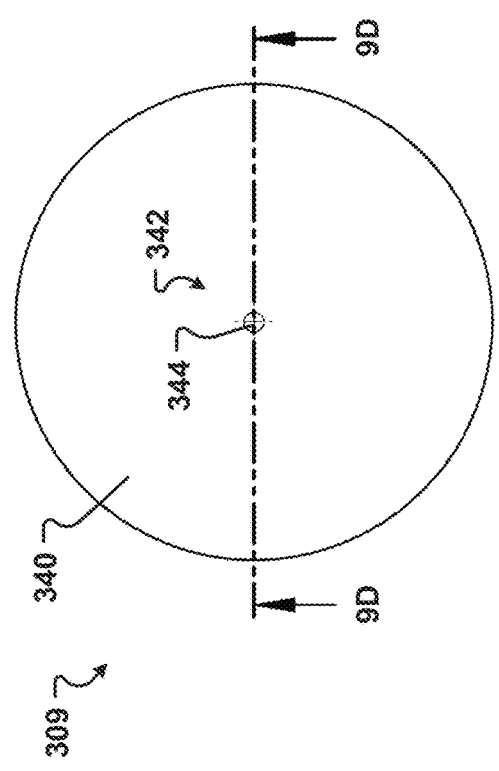
FIG. 9D is a cross-sectional side elevation view of the cone of the settler device taken along line 9D-9D of FIG. 9A.

As shown in FIGS. 9B, 9D, each cone 309 can include projections 313 configured to contact an adjacent cone to hold each successive cone 309 in a stack of cones at substantially an equal spacing. In one embodiment, the projections 313 extend inwardly from an interior surface of the body 340. The projections 313 are configured to contact an exterior surface of a body 340 of an adjacent cone. Alternatively, the projections 313 can extend from an exterior surface of the body 340.

The projections 313 may be sized to provide any desired spacing between adjacent cones. Optionally, the projections 313 are configured to separate adjacent cones by a distance between approximately 1 mm to approximately 2.5 cm. In exemplary embodiments, each cone 309 includes at least three projections 313.

Referring now to FIGS. 2 and 3, when the cones 309 are positioned within the upper housing 301A, the body 340 of the bottom cone 309A is supported by the second spacers 315B of the lower housing 301B. At least the conical portion 303 of the lower housing 301B and portions of the cylindrical portions 308A, 308B may be empty of cones. Accordingly, cells in culture can be retained in the settler device 300.

During operation of the settler device 300 of the embodiments depicted in FIGS. 1-9D, serum-free or animal protein-free cell culture medium may be pumped into the settler device 300 through one or more of the first and second ports 353, 354 of the lower housing 301B. The cell culture medium can be pumped continuously or periodically into the settler device 300. Specifically, the settler device 300 can operate in batch or continuous mode operation.

A controlled mixture of $O_2$, $CO_2$, and $N_2$ may also be pumped into the settler device 300 to control the pH and DO of the culture supernatant inside the settler device 300. Optionally, one or more of the second ports 354A, 354B and the lower housing 301B first port 353B can be used for sampling bioreactor contents, for example to check cell viability, and continuous measurement of liquid pH and DO for inputs into a computer-controlled multi-gas mass flow controller.

At the end of in vitro cell expansion, the concentrated settled cells collecting at the bottom of the settler device 300 within lower housing 301B can be harvested from first port 353B of the lower housing. Clarified culture fluid containing any metabolic waste products, such as ammonia and lactate, or gasses, along with any not-yet settled smaller dead cells and cell debris, may be removed through the first port 353A of the upper housing 301A.

Optionally, the settler device 300 can be used as a stand-alone bioreactor/cell sorter combination. Growth media may be added to the cell settler device through one or more of the first and second ports 353, 354. Accordingly, the settler device 300 may be used without a perfusion bioreactor.

In one embodiment, sensors may be positioned within the settler device 300. Optionally, the sensors may be arranged on an interior surface of one or more of the housings 301A, 301B. At least a portion of the housings 301 may comprise a plastic. In exemplary embodiments, the entire housing may be composed of plastic. In exemplary embodiments, the plastic is transparent or at least translucent. Optionally, at least a portion of the housing 301 is transparent or translucent. For example, a transparent or translucent material may be interconnected to an aperture in the housing 301 similar to a window. The transparent portion may comprise glass, plastic, or any other suitable material. The transparent portion may be formed of a material which is transparent to light of a predetermined range or ranges of wavelengths.

When present, the sensors are positioned to be in contact with media within the settler device 300. The sensors may be operable to monitor one or more of pH, DO, glucose, temperature, and $CO_2$ (including dissolved or partial $CO_2$) in the settler device 300.

Optionally, one or more of the sensors may comprise a fluorescent probe operable to emit light that varies based on a condition sensed by the fluorescent probe. Fluorescent probes may be arranged in a variety of different positions within the settler device 300. More specifically, fluorescent probes can be arranged to measure different conditions, or changes of conditions, at different areas within the cell settler device. Optionally, at least one fluorescent probe is affixed to an interior surface of the conical portion 303B of the lower housing 301B.

Light emitted by the fluorescent probes passes through the surface of housing 301 (or a transparent portion of the housing) and may be collected by a reader or meter. As described herein, the meter is operable to report or display levels of at least one of pH, DO, glucose, temperature, and $CO_2$ sensed by the fluorescent probes within the settler device 300. Optionally, light emitted by a fluorescent probe may be collected by an optional fiber cable and transmitted to the meter.

Referring now to FIGS. 10-15, another configuration of a settler device 400 of this disclosure, useful for settling cells or particles, is illustrated. The settler device 400 generally includes an upper housing 301 and a lower housing 401. The upper housing 301 includes a first stack of cones 309 and the lower housing 401 includes a second stack of cones 409. The upper housing 301 and cones 309 are the same as, or similar to, the housings 301 and cones 309 described in conjunction with FIGS. 1-9D.

The lower housing 401 generally includes a conical portion 403, a cylindrical portion 408, a first port 453 and a second port 454. The ports 453, 454 are configured to interconnect to a tubing line.

In one embodiment, the lower housing 401 is fixedly joined to the upper housing 301. For example, the lower housing and upper housing can be welded (including heat welding), glued together, or joined by another means known to those of skill in the art.

Alternatively, the lower housing 401 can optionally include a flange 418. The optional flange 418 is configured to releasably interconnect to an optional flange 318 of housing 301. Accordingly, the flange 418 may include hooked projections, protrusions, recesses, tabs, and depression that function similar to features of the flange 318. Optionally, spacers 415 may extend inwardly from the cylindrical portion 408.

Figure 13:
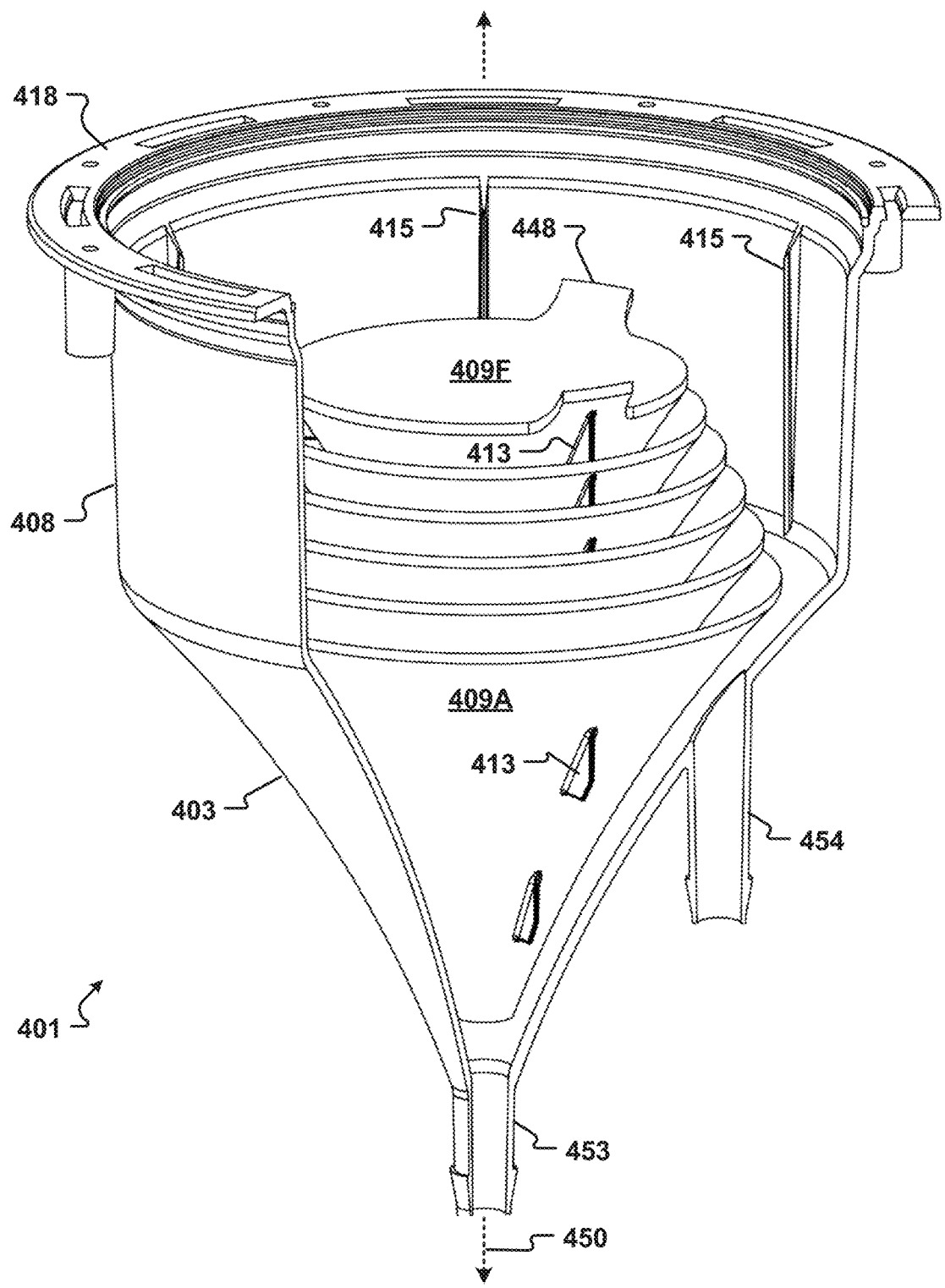
FIG. 13 is a partial cross-sectional perspective view of a lower housing of the settler device of FIG. 10 and showing the lower stack of cones.

Referring now to FIG. 13, the conical portion 403 of the housing 401 is convex inwardly towards the longitudinal axis 450. Specifically, a straight line drawn from a point of the conical portion proximate to the first port 453 to a point where the conical portion intersects the cylindrical portion 408 will lie outside of the housing 401.

The conical portion 403 can have a constant radius of curvature. Alternatively, the conical portion 403 can have two or more radii of curvature. For example, the conical portion 403 may have a first radius of curvature proximate to the cylindrical portion 408 and a second radius of curvature proximate to the first port 453. Center points of the first and second radii of curvature are positioned outside of the housing 401. In one embodiment, the conical portion 403 is sloped at an angle of less than approximately 45° relative to the longitudinal axis 450 at a point proximate to the first port 453. Optionally, at a point proximate to the cylindrical portion 408, the conical portion has a slope greater than approximately 45° to the longitudinal axis. In another embodiment, the slope of the conical portion 403 may vary between approximately 15° and approximately 85° relative to the longitudinal axis.

In exemplary embodiments, sensors may be positioned within the settler device 400. The sensors can be arranged on an interior surface of one or more of the housings 301, 401. The sensors may be arranged to be in contact with media within the settler device 400. The sensors are operable to monitor one or more of pH, DO, glucose, temperature, and $CO_2$ (including dissolved or partial $CO_2$) in the settler device 400. The sensors may be the same as other sensors described herein. Accordingly, one or more of the sensors may comprise a fluorescent probe operable to emit light that varies based on a condition sensed by the fluorescent probe. The light may be transmitted through a transparent portion of the housings 301, 401 or through a window in the housings.

As illustrated in FIGS. 12 and 13, cones 409 are stacked in the lower housing 401. The cones 409 are oriented with a small opening 444 positioned proximate to the first port 453. The body 440 of each cone 409 has a shape that generally corresponds to the shape of the housing conical portion 403. Specifically, the cone body 440 can have an arcuate shape corresponding to at least a portion of the conical portion of the housing. In exemplary embodiments, the cone bodies are convex inwardly towards the longitudinal axis 450. Optionally, the cone bodies have a constant radius of curvature. Alternatively, the cone bodies may have two or more radii of curvature. In one embodiment, the slope of the bodies can vary between approximately 5° and approximately 85° relative to the longitudinal axis.

Projections 413 may be formed on the cone body 440 such that adjacent cones are separated by a predetermined distance. In one embodiment, the projections 413 extend inwardly from an interior surface of the cone body. Additionally, or alternatively, projections 413 can optionally be formed on an exterior surface of the cone body. When the cones are stacked together, the projections 413 contact an interior surface of a lower cone such that adjacent cones are separated by the predetermined distance. The projections 413 of the lowermost cone 409A will contact an interior surface of the conical portion 403 when the cones are positioned in the housing 401. An uppermost cone 409E may optionally include projections 448 which extend beyond the large opening 446. As shown in FIG. 12, the projections 448 of the uppermost cone 409E can contact an interior surface of the lowermost cone 309A of the upper stack of cones 309. Contact between the projections 448 and the cone 309A prevents unintended or inadvertent movement of the stack of cones 409.

Figure 14:
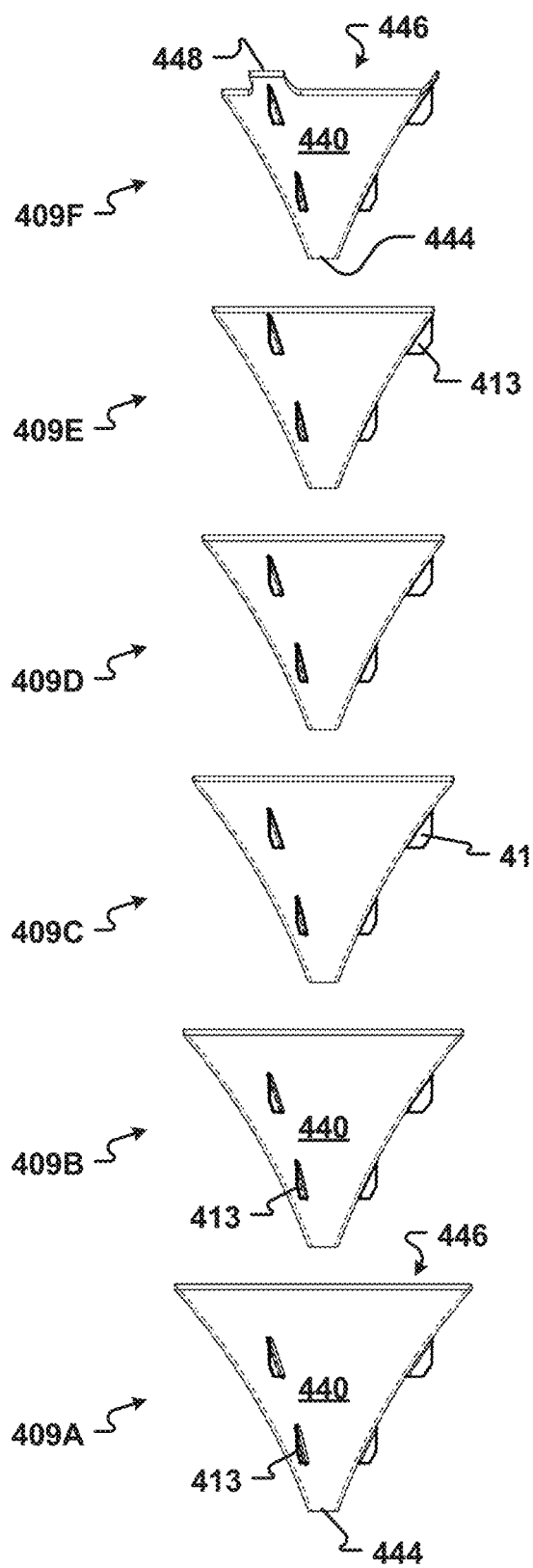
FIGS. 14 and 15 are views of the lower cones of the settler device of FIG. 10.
Figure 15:
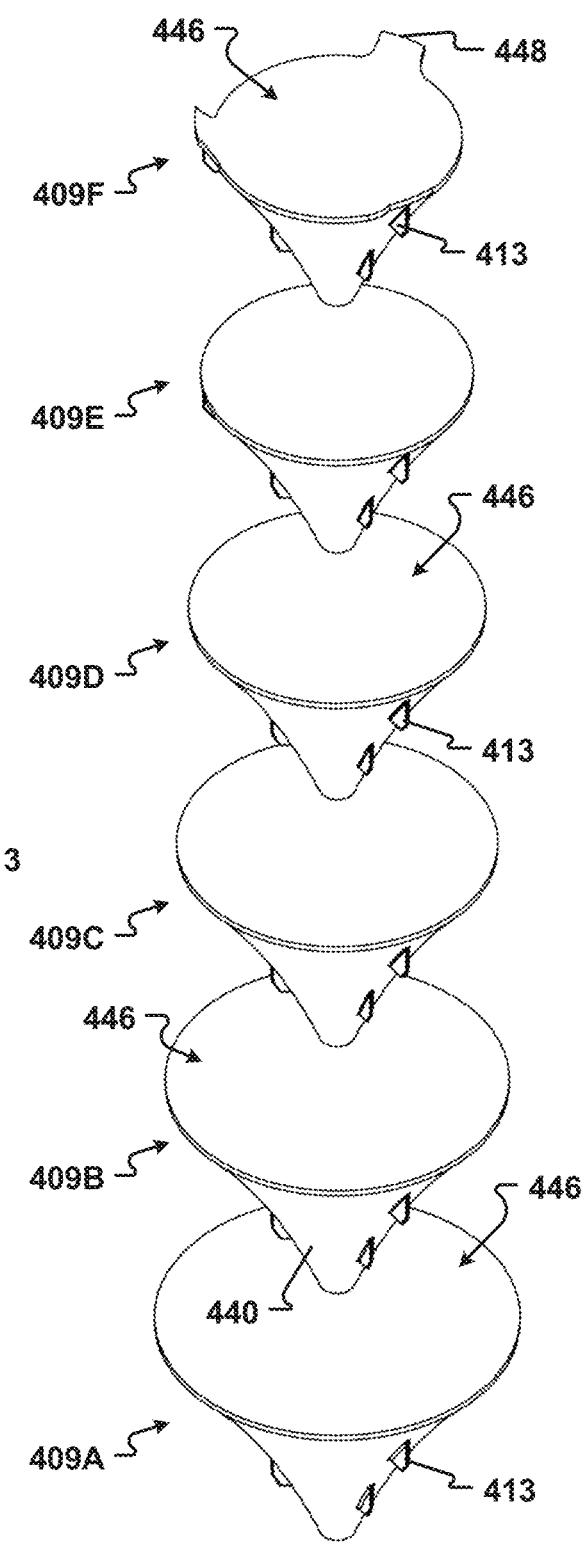

As illustrated in FIGS. 14 and 15, in some embodiments, the cones 409 have different diameters. A lowermost cone 409A may have a diameter that is larger than other cones in the stack. Each cone 409B-409E may have a successively smaller diameter with the uppermost cone 409E having the smallest diameter. In one embodiment, six cones 409A-409E may be stacked in the lower housing 401. In another embodiment, a stack of cones 409 in the lower housing may include from four to ten cones.

The settler device 400, including the housings 301, 401 and the cones 309, 409, can be formed of the same materials as other embodiments described herein. In exemplary embodiments, one or more of the housings and cones are fabricated of a single-use, disposable plastic. Alternatively, one or more of the housings and the cones are manufactured of a metal, such as a stainless-steel alloy, or a glass. Surfaces of the cones 309, 409, and interior surfaces of the housings 301, 401 may be completely or partially coated with one or more of a non-sticky plastic, teflon, silicone and similar materials known to those of skill in the art. Surfaces of the settler device 400 (especially when formed of stainless steel) may be electropolished to provide a smooth surface. The settler device 400 can be scaled to any desired size.

The settler device 400 may operate in the same or similar manner as settler device 300. Specifically, serum-free or animal protein-free cell culture medium may be pumped into the settler device 400 through one or more of the first and second ports 453, 454 of the lower housing 401. The cell culture medium can also be pumped continuously or periodically into the settler device 400. Specifically, the settler device 400 can operate in batch or continuous operation.

A controlled mixture of $O_2$, $CO_2$, and $N_2$ may also be pumped into the settler device 400 to control the pH and DO of the culture supernatant inside the cell settler device. Optionally, one or more of the second ports 354, 454 and the lower housing 301 first port 353 can be used for sampling bioreactor contents, for example to check cell viability, and continuous measurement of liquid pH and DO for inputs into a computer-controlled, multi-gas mass flow controller.

At the end of in vitro cell expansion, the concentrated settled cells collecting at the bottom of the settler device 400 can be harvested from first port 453 of the lower housing 401. Clarified culture fluid containing any metabolic waste products, such as ammonia and lactate, or gasses, along with any not-yet settled smaller dead cells and cell debris, may be removed through the first port 353 of the upper housing 301.

Optionally, the settler device 400 can be used as a stand-alone bioreactor/cell sorter combination. Growth media may be added to the cell settler device through one or more of the first and second ports 353, 354, 453, 454. Accordingly, the settler device 300 may be used without a perfusion bioreactor.

Referring now to FIGS. 16-21, another configuration of a settler device 500 for particles or cells of the present disclosure is illustrated. The settler device 500 includes elements that are the same as, or similar to, settler devices 300, 400 of the present disclosure. More specifically, the settler device 500 generally includes an upper conical portion 503A, a cylindrical portion 508, and a lower conical portion 503B which define a generally hollow interior. In one embodiment, the upper and lower conical portions 503A, 503B are substantially identical. At least one stack of cones 509 is positioned within the settler device 500.

The conical portions 503A, 503B generally include a first port 553 and optionally a second port 554. Optionally, the first port 553 is aligned substantially concentrically with a longitudinal axis 550 of the settler device 500. The first port 553 can be used as an inlet as well as an outlet.

The second port 554 can also be used to introduce or remove liquids, gases, and solids from the hollow interior of the settler device 500. In exemplary embodiments, the second port 554 extends through the conical portion 503. Optionally, the second port 554 can be aligned generally parallel to the longitudinal axis 550 of the cell settler device. In other embodiments, the second port 554 may extend through the cylindrical portion 508. In one embodiment, the second port 554 can be oriented transverse or perpendicular to the longitudinal axis 550. Other configurations of the first and second ports 553, 554 are contemplated. The settler device 500 may also have more than four ports.

The ports 553, 554 are configured to interconnect to a tubing line. Such tubing line may be interconnected to any of the compact cell settler devices of the present disclosure. The tubing line may have a diameter or otherwise be configured to interconnect to any port of embodiments of the present disclosure. The line may optionally include at least one sensor positioned within a hollow interior. The sensors may be in contact with fluid and/or particles within the line. Optionally, the sensors may be arranged on an interior surface of the line, although other configurations are contemplated. The sensors may be operable to monitor one or more of pH, DO, glucose, temperature, and $CO_2$ (including dissolved or partial $CO_2$) in the line.

Optionally, one or more of the sensors may comprise a fluorescent probe which emits light that varies based on a condition sensed by the probe. The light may be collected by a reader or meter. The light can optionally be collected by an optional fiber cable and transmitted to the meter. The meter is operable to report or display levels of at least one of pH, DO, glucose, temperature, and $CO_2$ sensed by the fluorescent probes. The line may comprise a material that is transparent or at least translucent. Thus, light generated by a sensor may pass through the line. Alternatively, at least a portion of a line is transparent or translucent, similar to a window. Accordingly, light generated by a sensor may be transmitted through window portion and collected by meter.

Figures 16, 17:
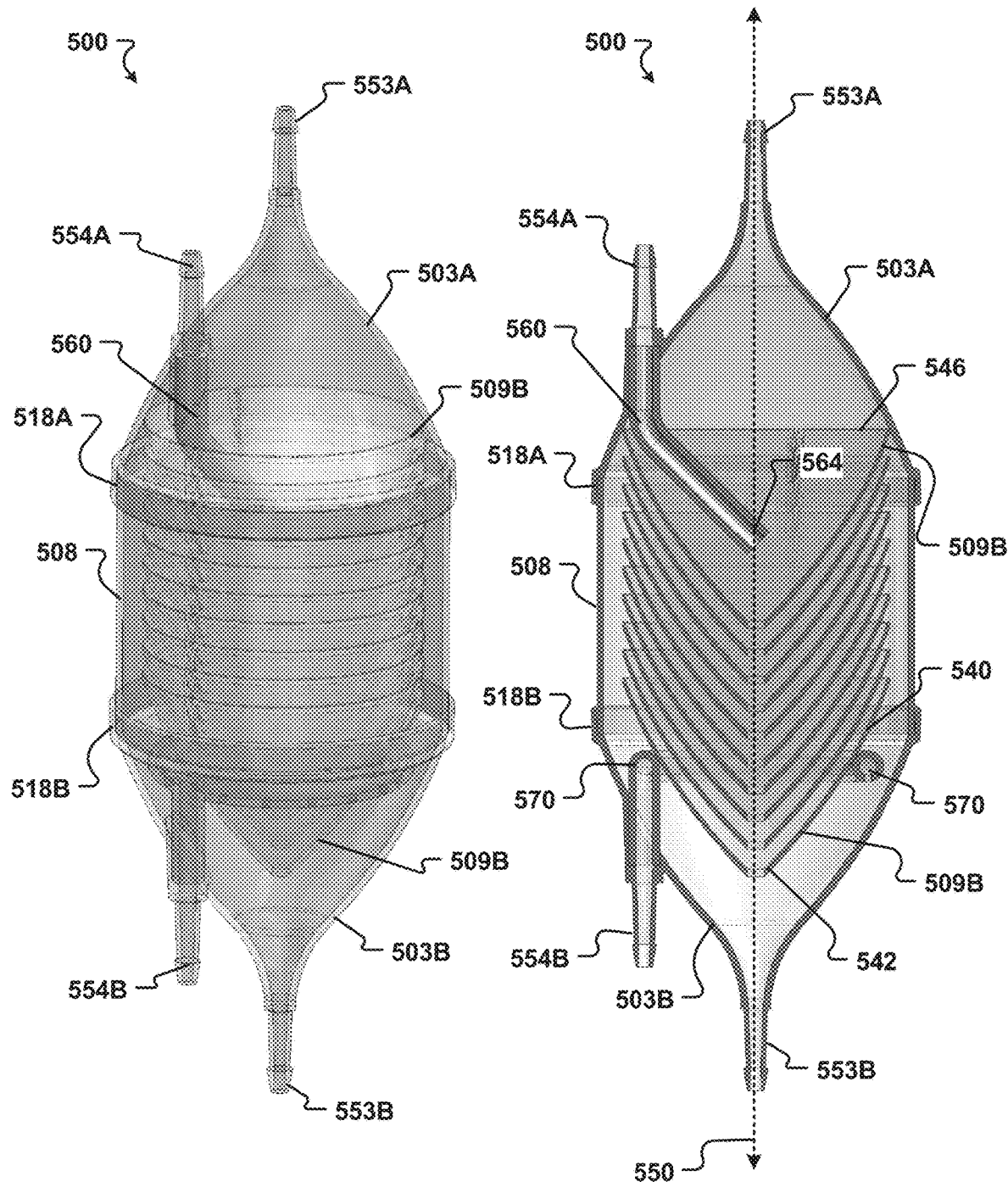
FIG. 16 is a front perspective view of a settler device of another configuration of this disclosure with internal elements of the settler device illustrated in phantom lines.
FIG. 17 is a cross-sectional front elevation view of the settler device of FIG. 16.
Figure 20B:
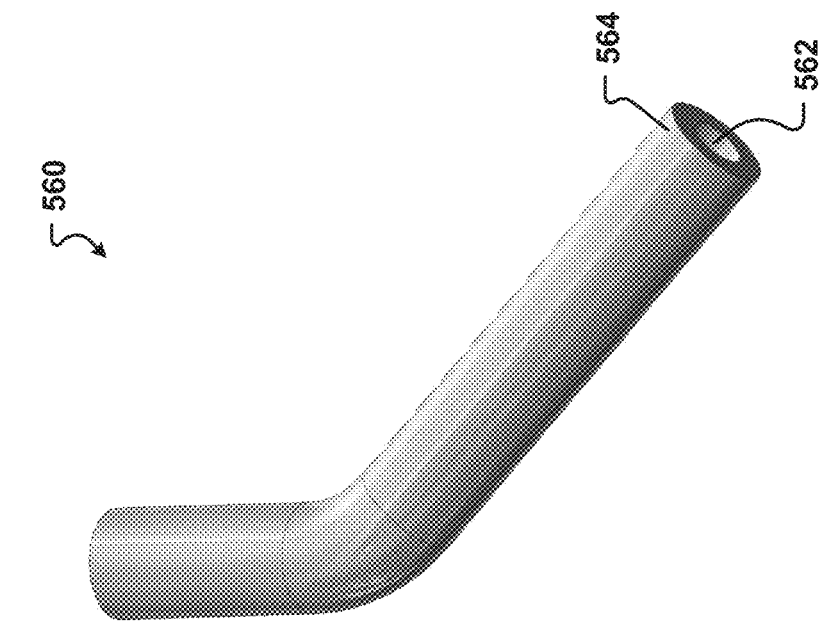
FIGS. 20A and 20B are perspective views of an optional conduit for use with settler devices of the present disclosure.
Figure 20A:
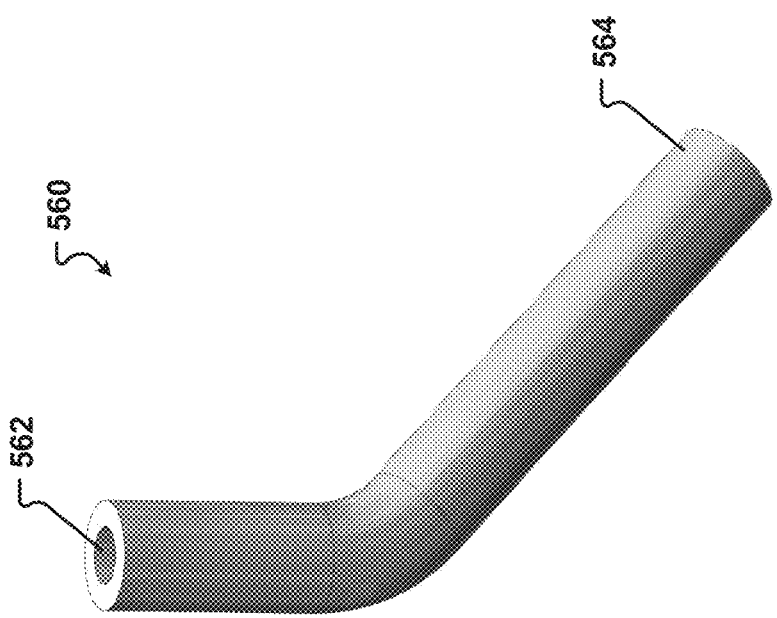

A conduit 560 can optionally be interconnected to at least one of the second ports 554 within the interior of the settler device 500. One embodiment of a conduit 560 of the present disclosure is generally illustrated in FIGS. 20A, 20B. A lumen 562 extends through the conduit. In one embodiment, the conduit 560 is not linear. More specifically, the conduit 560 can be bent. In this manner, the conduit is configured to extend inwardly within the settler device 500 with a free end 564 of the conduit positioned proximate to the longitudinal axis 550 as generally illustrated in FIG. 17. Accordingly, the lumen 562 through the conduit 560 can be positioned to inject or withdraw fluid from a medial portion of the settler device 500, such as from within an interior of a cone 509. In this manner, withdrawing fluid from the settler device 500 through the conduit 560 can facilitate the flow of fluid upwardly within the settler device such that cells or particles within the fluid settle onto the cones and migrate toward the lower conical portion 503B.

Figure 21A:
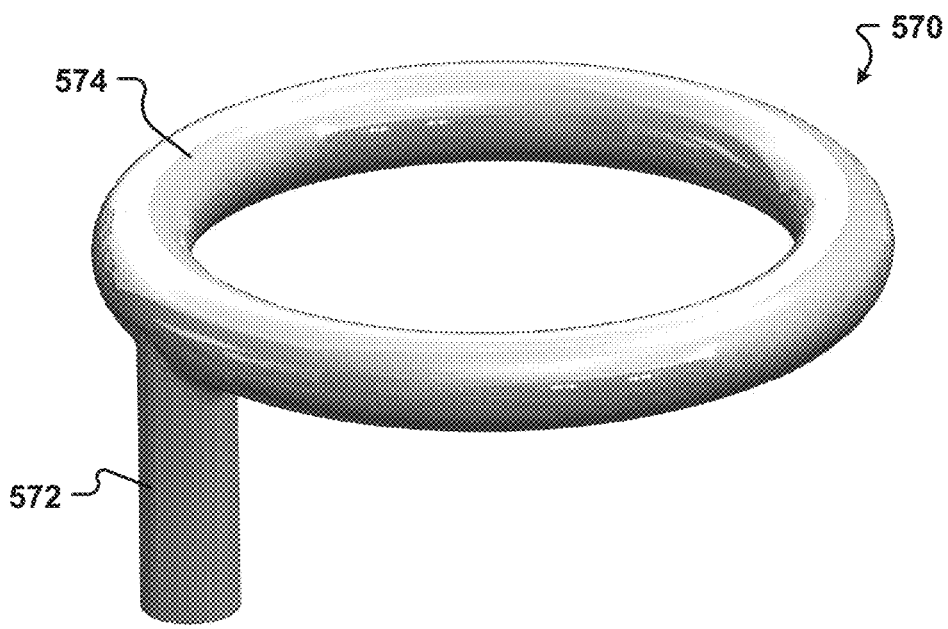
FIGS. 21A and 21B are perspective views that generally illustrate a diffuser of an embodiment of the present disclosure that is configured for use with settler devices.
Figure 21B:
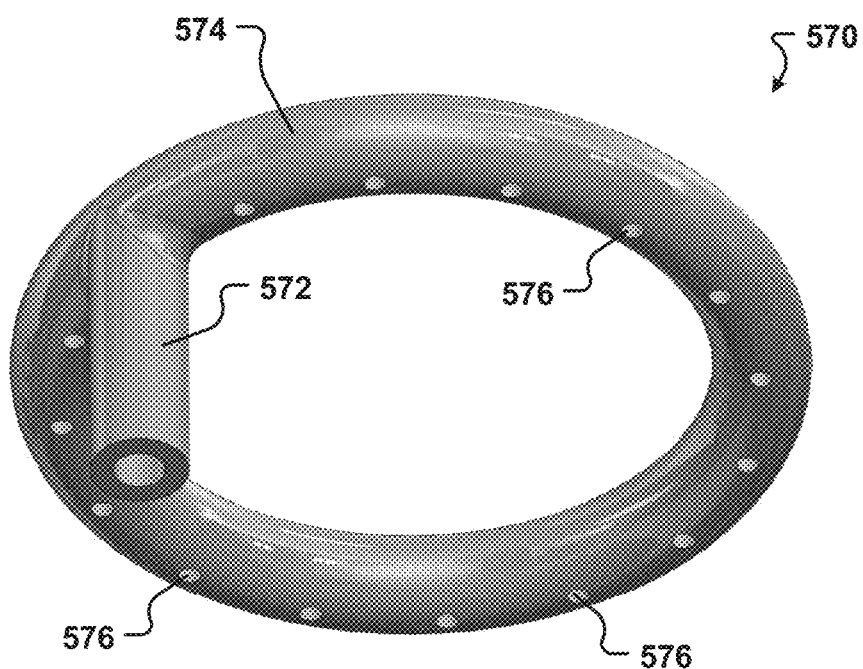

The settler device 500 can also include a diffuser 570 as generally illustrated in FIGS. 21A, 21B positioned within the hollow interior. The diffuser 570 can be associated with one of the second ports, such as the lower second port 554B. Fluid may be injected or withdrawn from the settler device 500 through the diffuser without disturbing particles or cells that have settled proximate to the lower conical portion 503B. When fluid is injected into the settler device 500 through the diffuser the fluid, which may contain cells or particles, is evenly distributed throughout the lower conical portion 503B of the settler.

Referring now to FIGS. 21A, 21B, the diffuser may comprise a torus or ring 574 extending from a stem 572. The stem 572 may be generally linear and configured to be oriented parallel to the longitudinal axis 550. The ring 574 can be configured to extend around the longitudinal axis 550 when the diffuser 570 is interconnected to the settler device 500. In one embodiment the ring 574 is adapted to be substantially concentric with the longitudinal axis.

An aperture 576 is formed through the ring 574 to facilitate transport of fluid, cells or particles through the diffuser. In one embodiment, the aperture 576 is formed on a side of the ring connected to the stem 572. In this manner, the aperture 576 can be oriented toward the lower first port 553B when the diffuser is interconnected to the lower second port 554. The aperture 576 can be configured as a single channel or groove. The groove may extend substantially continuously around the ring.

Alternatively, the ring can comprise a plurality of individual apertures 576. In one embodiment, the apertures are oriented axially to eject fluid generally parallel to the longitudinal axis. The apertures 576 may all be oriented in the same direction. Alternatively, some of the apertures can face different or opposite directions. Optionally, one or more of the apertures 576 can be oriented transverse to the longitudinal axis 550. Additionally, or alternatively, some of the apertures may be oriented radially or axially.

Referring again to FIG. 17, the cones 509 can be positioned within the settler device 500 and oriented to face one or more of the upper conical portion 503A and the lower conical portion 503B. In one embodiment, the settler device includes one stack of cones with a small end or apex 542 of the cones 509B oriented toward the lower first port 553B of the lower conical portion 503B. In this embodiment, a base or large opening 546 of the cones is oriented towards the upper first port 553A of the upper conical portion 503A. In exemplary embodiments, between three and twenty-five cones 509 are arranged in a stack within the settler device 500. In another embodiment, the stack includes from 6 to 14 cones, or 10 cones. However, the settler device 500 can be sized to receive any number of cones 509 when the settler device 500 is assembled as illustrated in FIGS. 16-17. At least a portion of the lower conical portion 503B may be empty of cones. More specifically, a lowermost cone 509 can be spaced a predetermined distance from an interior surface of the lower conical portion 503B. Accordingly, cells in culture can be retained in the settler device 500, for example, proximate to the lower first port 553B.

When the cones 509B are oriented with their apexes 542 proximate to the lower first port 553B, a body 540 of the bottom cone 509 can be supported by the diffuser 570. More specifically, as generally illustrated in FIG. 17, the bottom cone 509 may extend through the diffuser ring 574 such that the cone body 540 contacts the diffuser ring. The bottom cone can optionally be joined or welded to the diffuser ring. In this manner, the diffuser 570 is operable to position the bottom cone 509 a predetermined distance from the interior surface of the lower conical portion 503B.

Referring again to FIG. 17, optionally a flange 518 can extend from a large end of the conical portions 503 of the settler device. The flange 518 can have an interior diameter that is about equal to, but greater than, and exterior diameter of the cylindrical portion 508. In one embodiment, when the settler device is assembled, the flange 518 extends outside an exterior surface of the cylindrical portion 508 and approximately parallel to the longitudinal axis 550. The optional flange 518 is configured to interconnect an associated conical portion 503 to the cylindrical portion 508. For example, a conical portion 503 can be welded or otherwise fixed to the cylindrical portion 508 proximate to the flange 518.

Additionally, or alternatively, the flange 518 can include features adapted to align an associated conical portion 503 with the cylindrical portion 508. In an exemplary embodiment, the features comprise projections configured to engage corresponding recesses in the cylindrical portion.

The flange can be configured to retain a washer or a gasket positioned between the conical portion and the cylindrical portion. The gasket can be the same as, or similar to, gasket 338 generally illustrated in FIGS. 8A and 8B.

In one embodiment, one or more of the conical portions 503 of the settler device 500 are not linear. More specifically, the conical portions 503 can taper along an arcuate path from a maximum diameter proximate to the cylindrical portion 508 to a minimum diameter proximate to the first port 553. More specifically, and referring again to FIG. 17, a longitudinal cross-section of each of the conical portions 503 defines a line with an arcuate shape between the cylindrical portion 508 and the first port 553. In one embodiment, the conical portions 503 are concave inwardly towards a center of the settler device 500. In another embodiment, the conical portions 503 can have a constant radius of curvature. Optionally, in another embodiment, one or more of the conical portions 503 can have two or more radii of curvature. For example, a conical portion 503 may have a first radius of curvature proximate to the cylindrical portion 508 and a second radius of curvature proximate to an associated first port 553. Center points of the first and second radii of curvature are positioned within an interior of the settler device 500. Optionally, the slope of a conical portion 508 may vary between approximately 5° and approximately 85° relative to the longitudinal axis 550. In one embodiment, a conical portion 503 can include a convex portion proximate to the first port 553. The convex portion has a radius of curvature with a center point which is outside of the settler device 500.

Referring now to FIGS. 19A and 19B, the cones 509 generally include a body 540 having an apex 542 with a small opening 544 and a base with a large opening 546. Optionally, each of the cones is separately formed. In exemplary embodiments, the cones are of substantially the same size and shape.

In some embodiments, the body 540 may not be linear between the small and large openings 544, 546. As generally illustrated in FIG. 17, a longitudinal cross-section of the body 540 will form a line with an arcuate shape. The arcuate shape of each cone 509 may be approximately the same as one or more of the conical portions 503 of the settler device 500.

In some embodiments, the body 540 is concave inwardly toward the longitudinal axis 550. Thus, a straight line drawn from a point at the large opening 546 to a point at the small opening 544 is within an interior of the body.

Optionally, the body 540 has a constant radius of curvature. Alternatively, the body can have two or more radii of curvature. Thus, the body may have a first radius of curvature proximate to the small opening 544 and a second radius of curvature proximate to the large opening 546. Center points of the first and second radii of curvature are positioned within an interior of cone 509. In this manner, a portion of the body 540 proximate to the small opening 544 can have a slope that is different than a slope of the body proximate to the large opening. For example, proximate to the small opening 544, the body may be aligned at an angle of at least approximately 40° relative to the longitudinal axis 550. In contrast, near the large opening 546, the body can be closer to vertical (or closer to longitudinal axis). More specifically, the body may be sloped at an angle of less than approximately 45° relative to the longitudinal axis at a point proximate to the large opening 546. Optionally, the slope of the body 540 may vary between approximately 5° and approximately 85° relative to the longitudinal axis.

As shown in FIGS. 19A, 19B each cone 509 can include projections 513 configured to contact an adjacent cone to hold each successive cone 509 in a stack of cones at substantially an equal spacing. In one embodiment, the projections 513 extend outwardly from an exterior surface of the body 540. The projections 513 are configured to contact an interior surface of a body 540 of an adjacent cone. Alternatively, the projections 513 can extend from an interior surface of the body 340. In some embodiments, the projections 513 are oriented generally parallel to the longitudinal axis 550.

The projections 513 may be sized to provide any desired spacing between adjacent cones. Optionally, the projections 513 are configured to separate adjacent cones by a distance between approximately 1 mm to approximately 2.5 cm. In exemplary embodiments, each cone 509 includes at least three projections 513.

The projections 513 can optionally be configured to fix a first cone relative to a second cone. More specifically, the projection 513 can include a flange 532 and a groove 536. The groove 536 of a first cone can receive a flange 532 of a second adjacent cone as generally illustrated in FIG. 19A.

Figure 18:
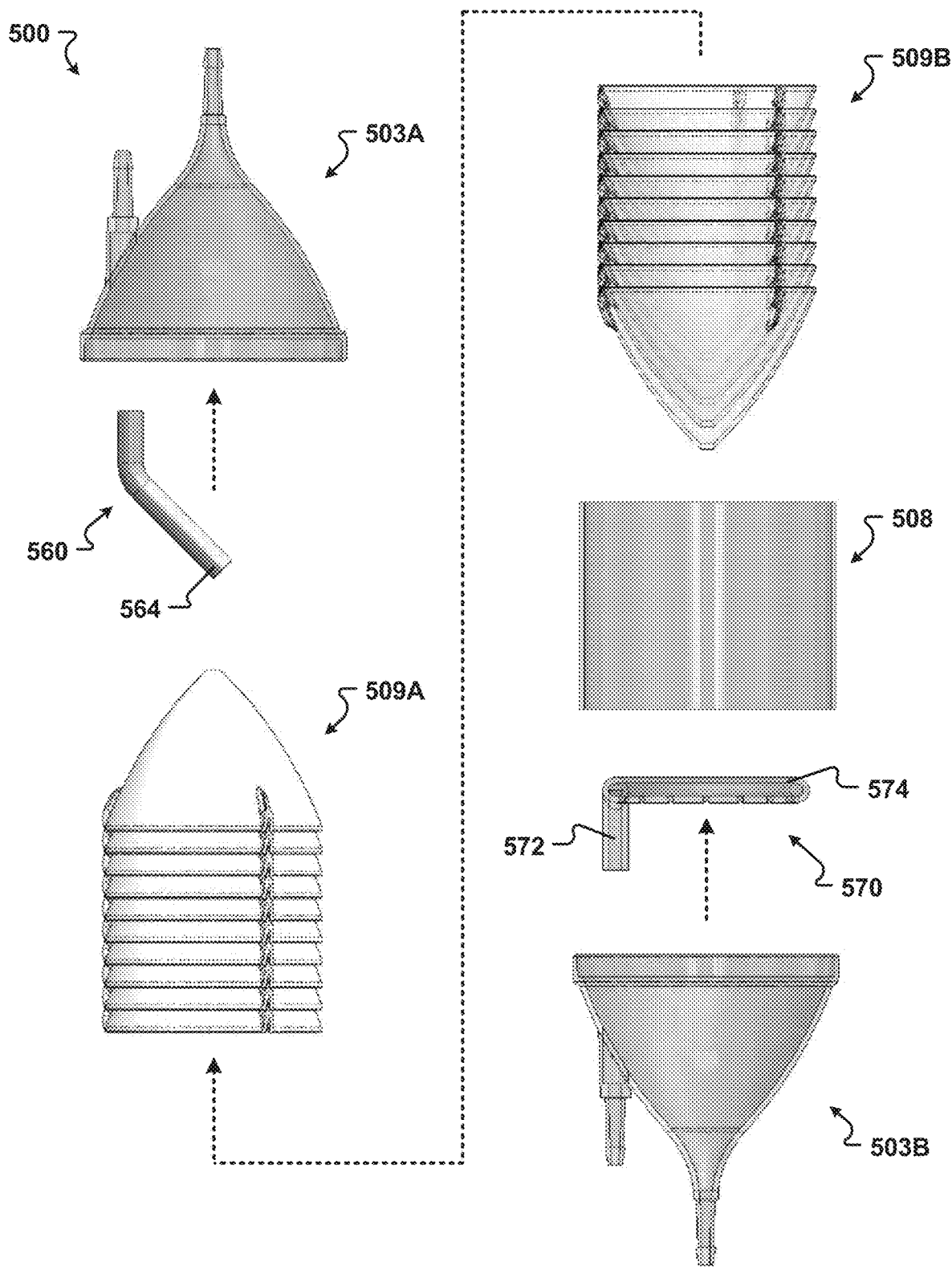
FIG. 18 an exploded front perspective view of the settler device of FIG. 16, illustrating an optional second set of cones adapted to be positioned within the settler device.

Referring now to FIG. 18, the settler device 500 can optionally include a second stack of cones 509A. Cones 509A of the second stack of cones may be the same as the cones 509B. Alternatively, the cones 509A may be of a different size or shape than the cones 509B. In one embodiment, the cones 509A of the second stack of cones may each be of a different size. For example, an uppermost one of the cones 509A can have a diameter that is greater than a lower one of cones. Similarly, a lowermost one of the cones 509A can have a diameter that is less than the other cones of the second stack of cones.

Optionally, one or more spacers (not illustrated) may project inwardly from an interior surface of the settling device 500. The spacers are configured to prevent the stack of cones 509 residing within the settler device 500 from resting against the interior surface of the conical portions 503 or the cylindrical portion 508. Optionally, the spacers can be approximately parallel to the longitudinal axis 550 of the settler device 300. The spacers may have a substantially thin cross-section to prevent or minimize interference with the movement or flow of liquid and suspended particles within the settler device 500. Although not illustrated in FIGS. 16-18, the spacers can be the same as, or similar to, the spacers 315 illustrated in FIGS. 5A, 5B, and 7 and described herein.

Elements of the settler device 500, such as the conical portions 503, the cylindrical portion 508, and the cones 509, can be fabricated of a single-use, disposable plastic. Alternatively, one or more of the conical portions 503, the cylindrical portion 508, and the cones 509 can be manufactured of a metal, such as a stainless-steel alloy, or glass. Surfaces of the cones 509, and interior surfaces of the conical portions 503 and the cylindrical portion 508 can be completely or partially coated with one or more of a non-sticky plastic, teflon, silicone and similar materials known to those of skill in the art. Additionally, or alternatively, the surfaces (especially when formed of stainless steel) may be electropolished to provide a smooth surface. These settler devices can be easily scaled to any desired size.

In one embodiment, the conical portions are fixedly joined to the cylindrical portion, for example, by a weld (such as a sonic weld or heat weld), an adhesive, or a glue. Optionally, one or more of the cones can by joined to an interior surface of the settler device. For example, in one embodiment, a portion of an uppermost cone 509 in the stack of cones can contact, and be fixed to, an interior surface of the upper conical portion 503A as generally illustrated in FIG. 17. In one embodiment, the cones can be joined together to form the stack of cones.

The settler device 500 can optionally include a fluid jacket (not illustrated). The fluid jacket can be associated with one or more of the conical portions 503 and the cylindrical portion 508. Water or other fluids may be directed into the fluid jacket through one or more ports to maintain the settler device 500 and its contents, including fluid therein, within a desired temperature range.

During operation of the settler device 500 of the embodiments depicted in FIGS. 16-18, serum-free or animal protein-free cell culture medium may be pumped into the settler device 300 through one or more of the first and second ports 553B, 554B of the lower conical portion 503B. The cell culture medium can be pumped continuously or periodically into the settler device 500. Specifically, the settler device 500 can operate in batch or continuous operation.

A controlled mixture of $O_2$, $CO_2$, and $N_2$ may also be pumped into the settler device 500 to control the pH and DO of the culture supernatant inside the settler device 500. Optionally, one or more of the second ports 554A, 554B and the lower conical portion 503B, and first port 553B, can be used for sampling bioreactor contents, for example to check cell viability, and continuous measurement of liquid pH and DO for inputs into a computer-controlled multi-gas mass flow controller.

At the end of in vitro cell expansion, the concentrated settled cells collecting at the bottom of the settler device 500 within the lower conical portion 503B can be harvested from first port 553B of the settler device 500. Clarified culture fluid containing any metabolic waste products, such as ammonia and lactate, or gasses, along with any not-yet settled smaller dead cells and cell debris, may be removed through the first port 553A of the upper conical portion 503A.

Optionally, the settler device 500 can be used as a stand-alone bioreactor/cell sorter combination. Growth media may be added to the cell settler device through one or more of the first and second ports 553, 554. Accordingly, the settler device 500 may be used without a connection to a perfusion bioreactor.

In one embodiment, sensors may be positioned within the settler device 500. Optionally, the sensors may be arranged on an interior surface of one or more of the conical portions 503 and the cylindrical portion 508. In exemplary embodiments, at least a portion of the settler device 500 may comprise a plastic. In exemplary embodiments, the entire housing may be composed of plastic. In exemplary embodiments, the plastic is transparent or at least translucent. Optionally, at least a portion of the settler device 500 is transparent or translucent. For example, a transparent or translucent material may be interconnected to an aperture in the settler device 500, similar to a window. The transparent portion may comprise glass, plastic, or any other suitable material. The transparent portion may be formed of a material which is transparent to light of a predetermined range or ranges of wavelengths.

When present, the sensors are positioned to be in contact with media within the settler device 500. The sensors may be operable to monitor one or more of pH, DO, glucose, temperature, and $CO_2$ (including dissolved or partial $CO_2$) in the settler device 500.

Optionally, one or more of the sensors may comprise a fluorescent probe operable to emit light that varies based on a condition sensed by the fluorescent probe. Fluorescent probes may be arranged in a variety of different positions within the settler device 500. More specifically, fluorescent probes can be arranged to measure different conditions, or changes of conditions, at different areas within the cell settler device. Optionally, at least one fluorescent probe is affixed to an interior surface of the lower conical portion 503B of the settler device.

Light emitted by the fluorescent probes passes through the surface of settler device (or a transparent portion of the settler device) and may be collected by a reader or meter. As described herein, the meter is operable to report or display levels of at least one of pH, DO, glucose, temperature, and $CO_2$ sensed by the fluorescent probes within the settler device 500. Optionally, light emitted by a fluorescent probe may be collected by an optional fiber cable and transmitted to the meter.

Figure 22:
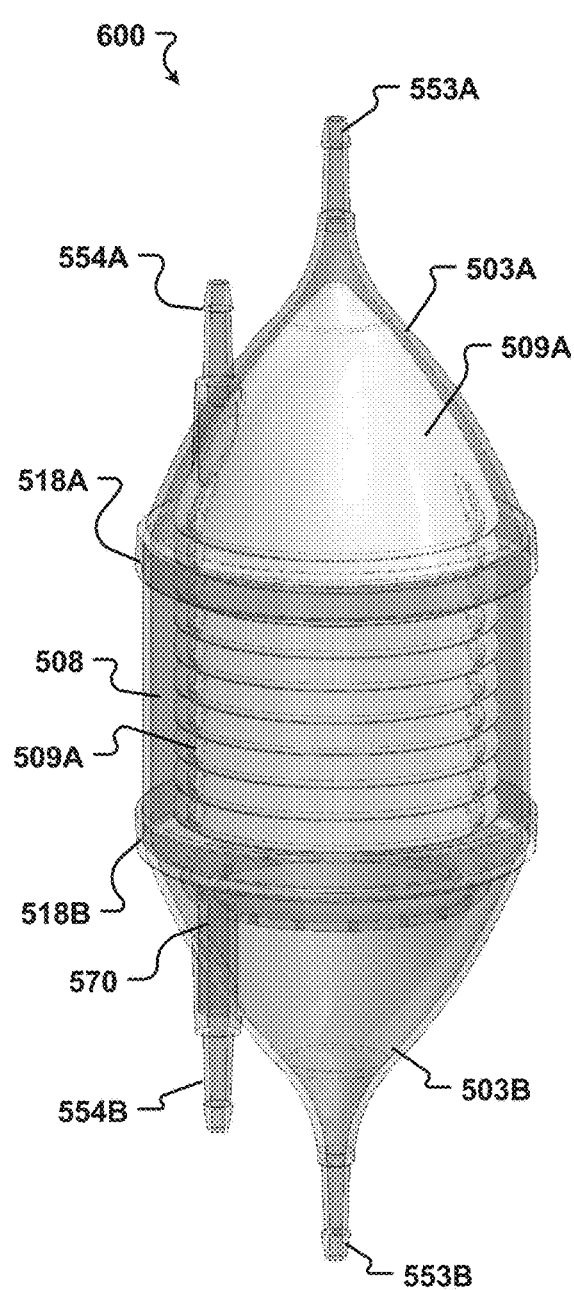
FIG. 22 is a front perspective view of another settler device of an embodiment of the present disclosure and illustrating some internal elements of the settler device in phantom lines.
Figure 23:
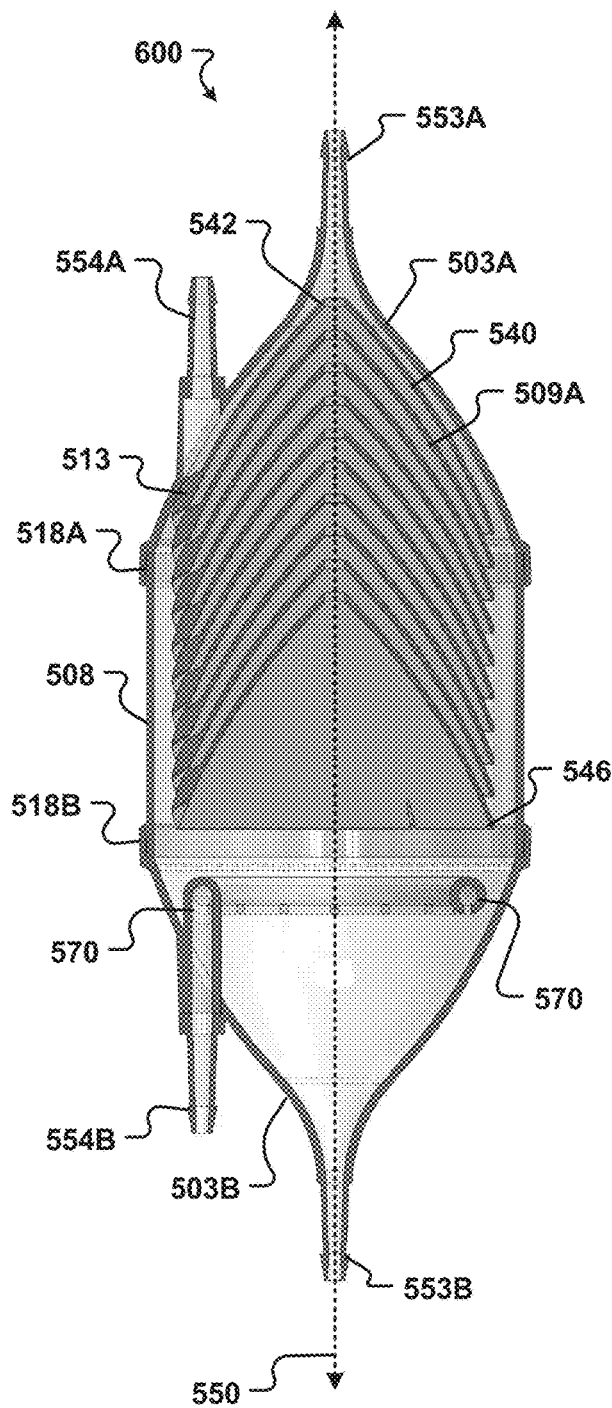
FIG. 23 is a cross-sectional front elevation view of the settler device of FIG. 22.

Referring now to FIGS. 22-23, another settler device 600 of the present disclosure is generally illustrated. The settler device 600 is similar to the settler device 500 and includes many of the same features. For example, the settler device 600 generally includes an upper conical portion 503A, a cylindrical portion 508, and a lower conical portion 503B that define a generally hollow interior. A diffuser 570 can be positioned within the hollow interior in fluid communication with a lower second port 553B.

A stack of cones 509A can be positioned within the settler device 600. Notably, the cones 509A are oriented with their apex 542 proximate to the upper conical portion 503A and a first upper port 553A.

The cones 509A may be fixed to an interior surface of the upper conical portion 503A. More specifically, in one embodiment, the cones include projections 513 as described herein. The projections 513 of an upper cone 509A can be fixed or welded to an interior surface of the upper conical portion 503A as generally illustrated in FIG. 23.

Optionally, a second stack of cones (not illustrated) can be positioned within the settler device 600. Cones of the second stack of cones can be oriented with their apexes proximate to the lower conical portion 503B. In one embodiment, the cones of the second stack of cones are the same as, or similar to, the cones 509A. Alternatively, the cones of the second stack of cones can be of a different size or shape than the cones 509A. In one embodiment, the second cones can have successively increasing diameters like the cones 409 illustrated in FIGS. 14 and 15.

In each of the embodiments of this disclosure, the angle of inclination of the surfaces of the conical surfaces of the stacked cones can be between about 30 degrees and about 60 degrees from the vertical. In certain embodiments, the angle of inclination for the surfaces of the conical surfaces or stacked cones is about 45 degrees from the vertical. In still another embodiment, the angle of inclination ranges between about 15 degrees and about 75 degrees. As described above, for the separation of stickier particles (typically mammalian cells), the angle of inclination is preferably closer to the vertical (i.e., about 30 degrees from the vertical). For less-sticky solid particles (for example, catalyst particles), the angle of inclination can be further from the vertical (preferably, about 60 degrees from vertical).

The material of construction of any of the settler devices of this disclosure, including the housing, the cones, and/or any additional components of the settler device, can be stainless steel (especially stainless steel 316), or similar materials used for applications in microbial or mammalian cell culture, as well as other metals used for applications in chemical process industries, such as catalyst separation and recycle. The stainless steel surfaces may be partially or completely electropolished to provide smooth surfaces that cells or particles may slide down after settling out of liquid suspension. Some or all of the surfaces of the settler device of this disclosure may be coated with a non-sticky plastic or silicone, such as dimethyldichlorosilane. Alternatively or additionally, the material construction of any of these settler devices of this disclosure may be non-metals, including plastics, such as single-use disposable plastics. While metal settling devices of the disclosure can be constructed via standard plate rolling and welding of steel angular plates to the bottom of the spiral plate, a plastic settler device of this disclosure, or individual parts thereof, may be more easily fabricated continuously as a single piece using, for example, injection molding or three-dimensional printing technologies.

In any of the settler devices of this disclosure, liquid may be directed into, or drawn out of, any of the ports or openings in the housing of the settling device by one or more pumps (for example a peristaltic pump) in liquid communication with the port or opening. Such pumps, or other means causing the liquid to flow into or out of the settler devices, may operate continuously or intermittently. If operated intermittently, during the period when the pump is off, settling of particles or cells occurs while the surrounding fluid is still. This allows those particles or cells that have already settled to slide down the inclined conical surfaces unhindered by the upward flow of liquid. Intermittent operation has the advantage that it can improve the speed at which the cells slide downwardly, thereby improving cell viability and productivity. In a specific embodiment, a pump is used to direct a liquid suspension of cells from a bioreactor or fermentation media into the settler devices of the present disclosure.

The thickness of the material constructing the cones placed within the housing of any of the settler devices of this disclosure is preferably as thin as necessary to maintain the rigidity of shape and to minimize the weight of the concentric stack of cones to be supported inside the housing. The radius and height of these devices can be scaled up independently as much as needed for the large-scale processes as may be calculated from predictive equations such as provided for inclined plate settlers (Batt et al. 1990, supra).

An important factor causing particle separation in the settler devices of this disclosure is the enhanced sedimentation on the inclined surfaces, which has been successfully demonstrated by Boycott (Nature, 104:532, 1920) with blood cells and on inclined rectangular surfaces as successfully demonstrated by Batt et al. (1990, supra) with hybridoma cells producing monoclonal antibodies. Additional factors enhancing the cell/particle separation are the centrifugal force on the cells/particles during their travel up the annular regions between successive cylinders and the settling due to gravity on the settling surfaces.

While lamellar plates have been used to scale up inclined plate settlers by each dimension independently, i.e. increasing the length, or the width or the number of plates stacked on top of each plate, the spiral conical settling zone can be scaled up in three dimensions simultaneously by simply increasing the horizontal radius of this device. As the horizontal radius of the device increases, the number of vertical and conical surfaces can be proportionally increased by keeping a constant distance (or channel width) between the successive spirals. The particle separation efficiency is directly proportional to the total projected horizontal area of the inclined settling surfaces. With an increase in device radius, the projected horizontal area increases proportional to the square of the radius, resulting in a three-dimensional scale up in the total projected area (i.e. proportional to the cube of radius) by simply increasing the radius.

The settler device 600 can operate in a manner similar to other settler devices of the present disclosure. For example, the settler device 600 can be used and operated as described in conjunction with the settler devices 300, 400, 500.

Methods of Use and Operation of Processes

Exemplary methods of using the settling devices of this disclosure are now described. A particle containing liquid (including, for example, cell culture liquid, waste water or reaction fluid containing solid catalyst particles, etc.) is introduced into a settler device of this disclosure though a port. Approximately 50%-99% of the entering liquid (typically about 90%) is removed through a port at the bottom of the settler device, while the remaining 1%-50% (typically about 10%) of the liquid is removed through a port at the top of the device. A pump (such as a peristaltic pump) may be used to suck liquid out of the top port, while the concentrated liquid exiting the bottom may be allowed to exit the bottom outlet of the cyclone housing due to gravity, without the need for a pump. Alternately, the liquid containing the settled cells or particles, may be pumped out from a bottom port of the conical settler at about 50%-99% of entering liquid flow rate, and the remaining clarified liquid (1-50%)

may exit via a top port. Optionally, fluid exiting the port may be pumped out into a harvest line.

Most of the entering cells (or particles) are pushed against the walls of the settler device assembly through centrifugal forces upon entry, settle down the conical portion through a gentle vortex motion initially, getting faster as the liquid and particles/cells go down and exit via the bottom port. Cells or particles which have not settled will move up through the stacks of cones. As the liquid moves slowly up through the stacks of cones, bigger particles (e.g., live cells) will settle on the surfaces of the cones and either slide down the cones or fall down the small spacing provided between the cones and the outer walls of the cyclone housing. These settled particles fall down vertically along the outer cylindrical walls until they reach the bottom conical section of the assembly and proceed to slide down the conical section to the bottom port.

By increasing the liquid inlet flow rate through port, it is possible to reduce the residence time of liquid inside the inclined settling zones such that smaller particles (for example dead cells and cellular debris) will not have settled by the time the liquid reaches the top of the settling zone, and therefore these smaller particles exit the settling device via the top port. This feature provides a simple method to remove smaller particles (such as dead cells and cellular debris) selectively via the top port into a harvest stream, while larger particles (such as live and productive cells) are returned from the bottom port to another vessel (such as a bioreactor).

Thus, in these methods, the step of introducing a liquid suspension into these settler devices may include directing a liquid suspension from a plastic bioreactor bag into the particle settling device.

Liquid may be directed into, or drawn out of, any ports or openings in the settling device by one or more pumps (for example a peristaltic pump) in liquid communication with the port or opening. Such pumps, or other means causing the liquid to flow into or out of the settler devices, may operate continuously or intermittently. If operated intermittently, during the period when the pump is off, settling of particles or cells occurs while the surrounding fluid is still. This allows those particles or cells that have already settled to slide down the inclined conical surfaces unhindered by the upward flow of liquid. Intermittent operation has the advantage that it can improve the speed at which the cells slide downwardly, thereby improving cell viability and productivity. In a specific embodiment, a pump is used to direct a liquid suspension of cells from a bioreactor or fermentation media into the settler devices of the present disclosure.

One parameter that may be adjusted in these methods of using the settler devices of this disclosure is the liquid flow rate into and out of the settler devices. The liquid flow rate will depend entirely on the particular application of the device and the rate can be varied in order to protect the particles being settled and separated from the clarified liquid. Specifically, the flow rate may need to be adjusted to protect the viability of living cells that may be separated in the settler devices of this disclosure and returned to a cell culture, but the flow rate should also be adjusted to prevent substantial cell or particle build up in the settler devices or clogging of the conduits that transfer liquid into and out of the settler devices.

In these methods, the clarified liquid collected from the settler device may include at least one of biological molecules, organic or inorganic compounds, chemical reactants, and chemical reaction products. The clarified liquid collected from the settler device may include at least one of hydrocarbons, polypeptides, proteins, alcohols, fatty acids, hormones, carbohydrates, antibodies, isoprenoids, biodiesel, and beer. In examples of these methods, the clarified liquid collected from the settler device includes at least one of insulin or its analogs, monoclonal antibodies, growth factors, sub-unit vaccines, viruses, virus-like particles, colony stimulating factors and erythropoietin (EPO).

Each publication or patent cited herein is incorporated herein by reference in its entirety. The settling devices of the present disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the present disclosure.

EXAMPLES

Example 1

Yeast or Other Microbial Cells Secreting Protein Products

Recombinant microbial cells, such as yeast or fungal (*Pichia pastoris, Saccharomyces cerevisiae, Kluyveromyces lactis, Aspergillus niger*, etc.) or bacterial (*Escherichia coli, Bacillus subtilis*, etc.) cells, which have been engineered to secrete heterologous proteins (for example, insulin or brazzein) or naturally secreting enzymes (e.g. *A. niger, B. subtilis*, etc.) can be grown in bioreactors attached to the compact settler devices of this disclosure, to recycle live and productive cells back to the bioreactor, which will thereby achieve high cell densities and high productivities. Fresh nutrient media is continuously supplied to the live and productive cells inside the high cell density bioreactors and the secreted proteins or enzymes are continuously harvested in the clarified outlet from the top port (or top-side outlets 353A, 354A, 553A, 554A), while the concentrated live and productive cells are returned back to the bioreactor. As dead cells and a small fraction of live cells are continuously removed from the bioreactor via the harvest outlet, cell growth and protein production can be maintained indefinitely, without any real need for terminating the bioreactor operation. In operations using yeast *Pichia* cells with the conical settler devices of this disclosure, the perfusion bioreactor has been operated for over a month. As the microbial cells grow in suspension culture and the cell retention device can be scaled up to any desired size, a settler of this disclosure can be attached to suspension bioreactors of sizes varying from lab scale (<1 liter) to industrial scale (>50,000 liters) or any size therebetween to achieve high cell density perfusion cultures.

In one specific example, a perfusion bioreactor culture of yeast *Pichia pastoris* cells is described. Yeast *Pichia pastoris* cells were grown in a 5-liter, computer-controlled bioreactor, initially in batch mode to grow the cells from the inoculum for the first 50 hours, then in fed-batch mode to fill up the attached 12-liter cell settler slowly for the next 100 hours, and then in continuous perfusion mode with a compact cell settler of this disclosure to remove the smaller dead cells and recycle the larger live cells back into the bioreactor.

Figure 24:
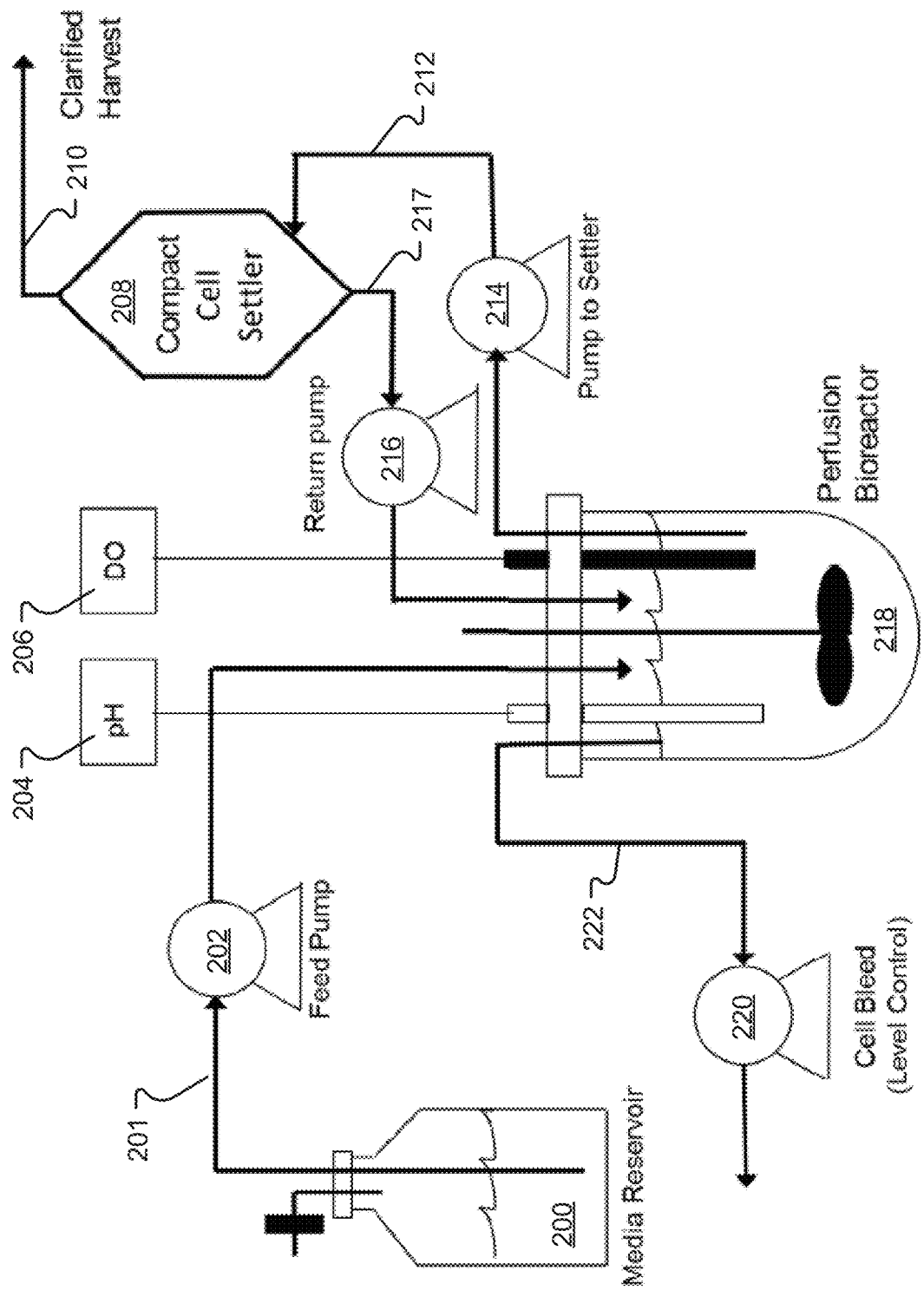
FIG. 24 is a schematic representation of the attachment of a compact cell/particle settler device of this disclosure to a modular bioreactor.

A typical schematic of the attachment of a compact cell/particle settler of this disclosure to any modular bioreactor is depicted in FIG. 24.

Referring to FIG. 24, the yeast *Pichia pastoris* cells were grown in a perfusion bioreactor (218). Growth media was added to the bioreactor (218) from media reservoir (200) via a first pump (202) interconnected to input line (201). Dissolved oxygen content and pH were continuously monitored in the bioreactor (218) by dissolved oxygen monitor (206) and pH monitor (204). Yeast cell culture from the bioreactor (218) was delivered to a 12-liter compact cell settler (208) of the present disclosure via a second pump (214) interconnect to line (212). Effluent from the compact cell settler (208), which contained smaller dead cells, was evacuated by effluent line (210). Larger live cells were recycled from the cell settler (208) back to the bioreactor (218) via third pump (216) and return line (217). Media and cell culture levels in the bioreactor (218) were controlled by removing excess cell culture via fourth pump (220) and removal line (222) to be captured or discarded.

Figure 25:
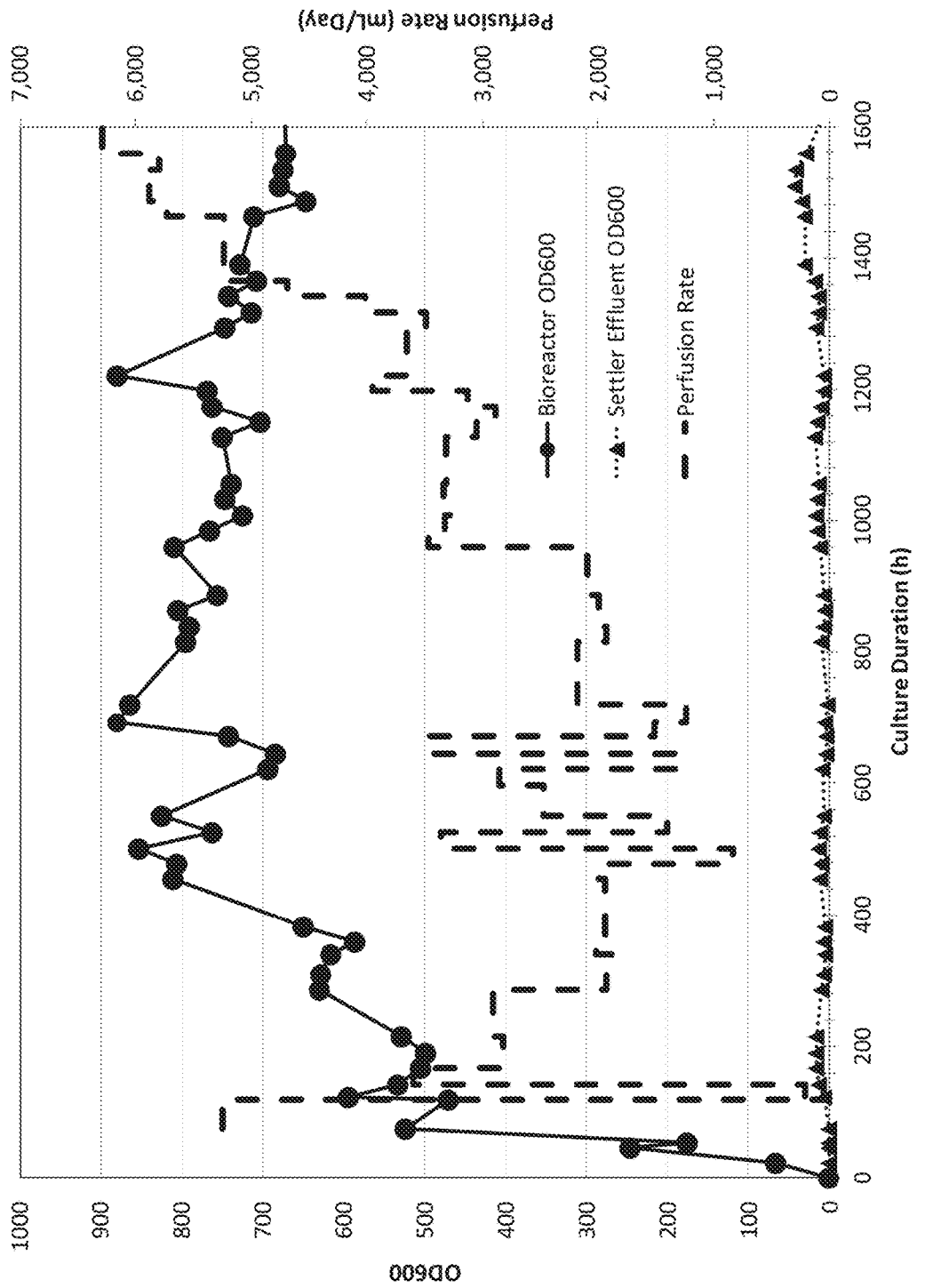
FIG. 25 is a graph which shows results of perfusion bioreactor culture of yeast *P. pastoris* cells, with a fully packed compact cell settler as the cell retention device and set up as depicted in FIG. 24.

Results obtained with this perfusion bioreactor set up with a compact cell/particle settler of this disclosure are shown in FIG. 25. The circles show the optical density of bioreactor samples, measured at 600 nm, building up during the initial batch and fed-batch culture period of about 150 hours, followed by continuous perfusion operation up to 1600 hours or longer than 2 months. The settler effluent or harvest rate is adjusted by manipulating either settler inlet pump setting and/or settler recycle pump setting. The cell concentration (as measured by OD at 600 nm) and the size distribution are determined by the harvest flow rate and cell size distribution of the cells entering from the bioreactor and other factors such as the recycle ratio from the settler. The effluent stream contains very little cells, as measured by the very low OD's in the range from 0 to 30, even as the perfusion rate is gradually increased from 2000 ml/day to over 6,000 ml/day. These results demonstrate that very high cell density was obtained and maintained in the bioreactor due to the recycle of most of the live cells back to the bioreactor and selective removal of smaller dead cells and cell debris. Even at these increasing perfusion rates, the bioreactor can be operated indefinitely at high cell density without any reason to terminate the bioreactor, such as clogged membranes in competing membrane-based cell retention devices.

Figure 26:
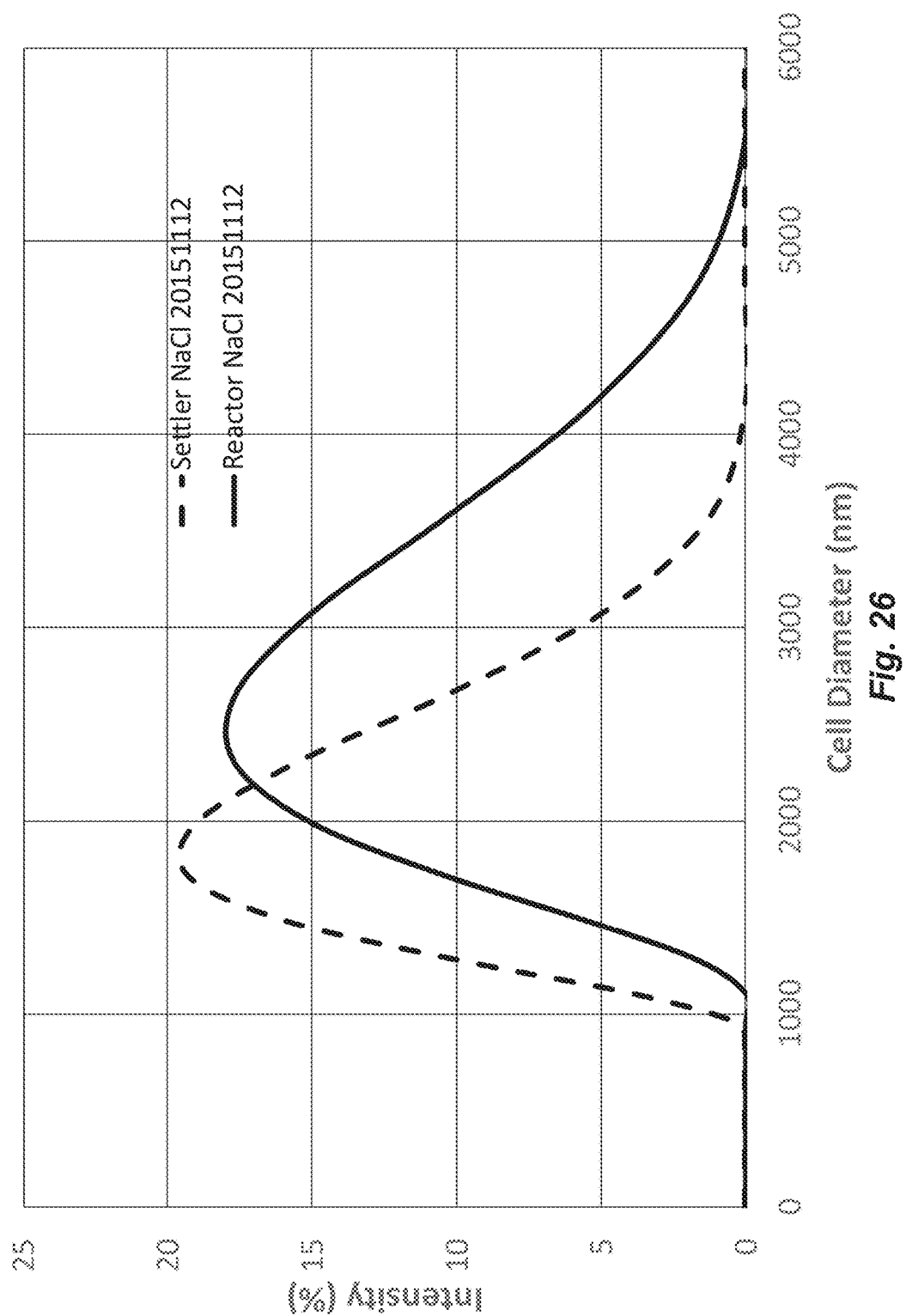
FIG. 26 shows particle size analysis of samples taken from the bioreactor and settler effluent from the apparatus set up as depicted in FIG. 24.

Samples from the bioreactor and settler effluent taken at the same time point were analyzed with a particle size analyzer. The normalized cell size distribution results shown in FIG. 26 clearly indicate that the settler effluent contains a significantly smaller cell size distribution compared to that found for the cells in the bioreactor. These results demonstrate that the settler removed the smaller dead cells and any cell debris preferentially in the effluent, while the larger live cells are preferentially returned to the bioreactor. Thus, the bioreactor is continuously cleaned by selective removal of dead cells and cell debris by the settler effluent and consequently there is no accumulation of dead cells and cell debris within the bioreactor, as happens routinely with all other cell retention devices.

The bioreactor and settler effluent samples from an early time point during the perfusion culture were collected and centrifuged in small 2 ml vials. Cells pelleted from effluent from the settler device (208) and cells pelleted from within the bioreactor (218) showed that he pelleted cells from the bioreactor (218) occupy almost 50% of the wet packed cell volume in the vial, while the pelleted cells in the settler effluent occupy only about 5% of the wet packed cell volume. These results again confirm that only a very small fraction of the intact smaller cells from the bioreactor are removed in settler effluent while most of the larger intact cells are preferentially returned to the bioreactor.

Total protein concentrations in the bioreactor and settler effluent during this 2-month long perfusion operation were measured and showed that after the initial batch and fed-batch operation, i.e. during the prolonged perfusion operation, total protein content in the effluent sample from the settler device (208) is consistently greater than the total protein content in the sample from the bioreactor (218). These results suggest very strongly that there is no protein sieving inside the settler (208), as is commonly observed with membrane-based cell retention devices such as ATF in perfusion cultures of mammalian cells. Further, these results suggest that there is some additional protein production in the settler (208), causing the effluent protein concentrations to be consistently higher than those in the bioreactor (218) at the same time.

The total accumulated protein in the harvest stream from the continuous perfusion bioreactor configuration illustrated in FIG. 24 can be compared with protein can be harvested in the cell-free supernatant of a single fed-batch bioreactor (218) performed over 158 hours or almost 6 days, and repeated again and again over the same culture duration of say 1600 hours. While fed-batch cultures typically have a long downtime to harvest or empty the bioreactor, clean the internal surfaces, sterilize in situ with steam, cool, refill the bioreactor with sterile medium, inoculate the bioreactor with fresh cells and then allow the cells to grow to high enough cell density to see significant increase in the protein titer, the continuous perfusion bioreactor continues to operate uninterrupted at high cell density and high production rate throughout the culture operation. Consequently, the total accumulated protein in the continuously harvested product stream is increasing, at a significantly faster rate as the perfusion rate is increased, and accumulates to 160 g, 5× higher protein amount than can be harvested in the cell-free supernatants from 8 repeated fed-batch culture operations in the same 5 liter bioreactor.

Example 2

Removing Yeast Cells from Beer

In large-scale brewing operations, yeast cells are removed from the product beer by filtration devices, which regularly get clogged, or centrifugation devices, which are expensive high-speed mechanical devices. Previously, hydrocyclones were unsuccessfully tested for this application (Yuan et al., 1996; Cilliers and Harrison, 1997). These devices can be readily replaced by the settler devices of this disclosure to clarify beer from the top outlets and remove the concentrated yeast cell suspension from the bottom outlet. Due to the increased residence time and enhanced sedimentation in the conical settler zones of this disclosure, the inventor has achieved successful separation of yeast cells from cell culture liquid, harvesting the culture supernatant containing only about 5% of the cells entering the settler device in its first operation. As the device can be scaled up or down to increase or decrease its cell separation efficiency, it is feasible to obtain completely cell-free beer from the harvest port, if desired. Thus, the devices of this disclosure may be particularly useful in brewing beer, as well as clarifying beer, and in continuous brewing arrangements.

Example 3

Clarifying or Removing Cells from Mammalian Cell Culture Broth

Similar to example 2 above, clarification of mammalian cells from cell culture broth at the end of a fed-batch bioreactor culture is a necessary first step in the harvest of the secreted product, such as antibodies or therapeutic glycoproteins, to be followed by a series of other downstream processing operations. Currently, centrifugation and depth filtration are used as the common unit operations to remove mammalian cells and cell debris from the cell culture broth. However, periodic removal of accumulated cells from the continuous centrifugation process results in repeated cloudburst of cells into the clarified cell culture supernatant. The settler devices of the present disclosure produce a continuously clarified (cell-free or significantly depleted in cells) supernatant as the mammalian cells are easily settled inside the device. These compact settler devices offer a more consistent removal of cells from the cell culture broth, potentially replacing the need for any centrifugation and reducing the amount of membrane area needed in a secondary depth filter operation to completely eliminate any remaining cells and all cell debris. The clarification can be in batch operations or in continuous operations in perfusion bioreactors as described below.

Example 4

Mammalian Cell Perfusion Cultures

Enhanced sedimentation of murine hybridoma and recombinant mammalian cells in inclined settlers have already been demonstrated successfully (Batt et al., 1990 and Searles et al., 1994) and scaled up in lamellar settlers (Thompson and Wilson, U.S. Pat. No. 5,817,505). While the lamellar settlers are scaled up in three dimensions independently, a conical settler device of this disclosure can be scaled up in three dimensions simultaneously by simply increasing its radius, as discussed above. Thus, the settlers of this disclosure are more compact, contain much more inclined surfaces for settling on a smaller footprint, and are more easily scalable cell retention devices with proven applications in mammalian cell cultures secreting glycoproteins, such as monoclonal antibodies, and other therapeutic proteins. The clarified harvest output from the top port containing the secreted protein is harvested continuously from the cell retention device, while the concentrated cells from the bottom outlet are recycled back to the bioreactor, resulting in a high cell density perfusion bioreactor, that can be operated indefinitely, (i.e. over several months of continuous perfusion operation). The continuous high titer harvest from a single, 1000-liter, high cell density perfusion bioreactor can be more than the accumulated production from a large (>20,000 liter) fed-batch bioreactor on an annual basis.

Recombinant Chinese hamster ovary cells, which are used commonly in the overexpression and secretion of therapeutic glycoproteins, are cultured in a 1-liter controlled bioreactor attached with a 4" compact cell settler as shown schematically in FIG. 24. Viable cell densities in the bioreactor, settler top effluent, and settler bottom return to the bioreactor were measured. Soon after the perfusion operation starts at 60 hours, very few live cells are removed from the settler top effluent and increasing amounts of viable cells are being returned to the bioreactor from the settler bottom outlet. Consequently, the bioreactor viable cell density (VCD) is increasing gradually after the perfusion operation begins and more dramatically the viability percentage (diamonds) in the bioreactor increases when the perfusion begins.

Cell size distributions were measured on samples from the bioreactor and settler top effluent on day 5 and a histogram of cell/particle sizes measured by a Beckman-Coulter Multisize Analyzer for the bioreactor sample shows a broad distribution of live cells and possibly doublets in sizes ranging from about 10 microns to about 30 microns with a peak of about 16 microns, a sharp peak of dead cells in sizes between 8 and 9 microns and huge tail of cell debris in the smaller size range smaller than 8 microns. Another histogram of cell/particle sized measured by the same instrument on the sample from the top port effluent of the compact cell settler (208), showed an enhanced peak of dead cells in size between 8 and 9 microns, a tail of cell debris in the sizes smaller than 8 microns and dramatically a total absence of any peak for live cells about 16 microns. These size measurements strongly demonstrate that settler top effluent removes selectively the smaller dead cells and cell debris from the perfusion bioreactor (218), while the larger live cells are continuously returned to the perfusion bioreactor (218). This selective removal of smaller dead cells and cell debris has been demonstrated (Batt et al. 1990 and Searles et al. 1994) with inclined plate settlers. The present disclosure of compact cell settlers again reproduced those successive results in a more compact and more easily scalable design. None of the other cell retention devices available today for mammalian cells exhibit any such selectivity in removing only the smaller dead cells and cell debris.

Example 5

Vaccines, Viruses or Virus-Like Particles or Gene Therapy Vector Production Production of vaccines, such as viruses or virus-like particles (VLPs), or gene therapy vectors, such as adeno-associated viruses (AAV), lenti-viruses, etc. is usually carried out by infection and lysis of live mammalian or insect cells in a batch or fed-batch bioreactor culture. Viruses or virus-like particles are released from the infected cell in a lytic process after large intracellular production of these viruses or virus-like particles. With the large difference in the size (sub-micron or nanometer scale) of these particles compared to the size (about 5-20 microns) of live mammalian and insect cells, the separation of the viruses or virus-like particles from the batch or fed-batch bioreactor culture is very simple. By controlling the continuous harvest or outlet rate of clarified cell culture broth containing mostly viruses or VLPs, along with cell debris, it is also possible to retain a smaller number of the infective particles inside the bioreactor along with the growing live cells to continually infect and produce vaccines in a continuous perfusion bioreactor attached to a settler device of this disclosure for continuous harvest of viruses and VLPs.

Example 6

Solid Catalyst Particle Separation and Recycle

Separation of a solid catalyst particle for recycle into the reactor and reuse in further catalyzing liquid phase chemical reactions, such as Fischer-Tropsch synthesis, has been demonstrated before with lamellar settlers (U.S. Pat. No. 6,720, 358, 2001). Many such two-phase chemical reactions, involving solid catalyst particles in liquid or gas phase reactions can be enhanced by the particle settling devices of this disclosure, which presents a more compact particle separation device to accomplish the same solids separation and recycle as demonstrated with lamellar settlers.

Example 7

Plant and Algal Cell Harvesting

Recombinant plant cell cultures secreting valuable products, while not yet commercially viable, are yet another field of potential applications for the settling devices of this disclosure. Inclined settlers have been used in several plant cell culture applications. Such devices can be replaced by the more compact conical spiral settler devices of this disclosure. With the size of plant cells being higher than those of yeast or mammalian cells, the cell separation efficiency will be higher with single plant cells or plant tissue cultures.

A more immediate commercial application of the settler devices of this disclosure may be in the harvesting of algal cells from large scale cultivation ponds to harvest biodiesel products from inside algal cells. Relatively dilute algal cell mass in large (acre sized) shallow ponds converting solar energy into intracellular fat or fatty acid storage can be harvested easily through the conical spiral settler device of this disclosure, and the concentrated algal cells can be harvested from the bottom outlet.

Example 8

Municipal Waste Water Treatment

Large scale municipal waste water treatment plants (using activated sludge or consortia of multiple bacterial species for degradation of biological and organic waste in sewage or waste water) commonly use large settling tanks and more modern versions of these plants use lamellar settlers to remove the clarified water from the sludge. The conical spiral settler devices of this disclosure can be scaled up to the larger sizes required in these plants, while remaining smaller in size than the large settling tanks or lamellar settlers currently used in these treatment plants.

Example 9

Industrial Process Water Clarification

Large scale water treatment plants, cleaning either industrial waste water or natural sources of turbid water containing suspended solids, use large scale settling tanks or lamellar inclined settlers. These large-scale devices can now be replaced with the more compact conical spiral settler devices of this disclosure to accomplish the same goal of clarifying water for industrial reuse or municipal supply of fresh water.

Example 10

Capture and Purification of Monoclonal Antibodies on Protein a Coated Beads

Cell culture supernatants containing monoclonal antibodies can be contacted with protein A coated microspheres or beads (40-200 microns) inside our settler via two different inlets, e.g. beads coming in from a top inlet and the cell culture supernatant coming in via the bottom port to maximize their contacting and capture efficiency. Capture of monoclonal antibodies on protein A beads is very quick, typically under 10 min. of residence time inside the competing affinity chromatography columns. The protein A-coated microspheric beads will settle down fast and can be kept in suspension and well mixed to contact with the cell culture supernatant by pumping it in from the bottom inlet. The depleted cell culture supernatants can be removed continuously from the top outlet of cell settlers of the present disclosure in a batch loading operation. Any beads entrained with upward-flowing liquid will settle on the inclined surfaces and return to the bottom stirred region. After loading close to the maximum binding capacity of the add beads, beads can be washed with the typical washing solution of about 3-5× volume of the settler to remove unbound host cell protein along with dead cell debris which are present in the supernatant via the top outlet.

After completing thorough washing, elution media will be pumped in slowly to remove the bound antibodies into the liquid medium and concentrated antibody solution is removed via the top port, while retaining the beads inside the settler. After elution is completed, equilibration of the beads is conducted by pumping in the equilibration solution from the bottom inlet, while the beads are held in suspension by this incoming solution. After equilibration, next batch of cell culture supernatant is loaded into the settler to repeat the above four-step process, similar to the sequence used in a chromatography column. Some advantages of using the cell settler devices of the present disclosure for monoclonal antibody capture are that: (i) cell culture supernatant can be directly loaded to contact with the protein A beads, without the need for removing dead cells or cell debris commonly present in the supernatant; and (ii) more efficient immediate contacting of all the suspended beads with in the incoming supernatant, rather than the gradual or delayed exposure of monoclonal antibodies to the fixed bed of beads in the later parts of the column. Elimination of currently required unit operations of centrifugation and/or depth filtration to remove dead cells and cell debris will result in significant cost savings, when the affinity column chromatography is replaced with affinity capture of antibodies by protein A beads suspended inside settler devices of embodiments of the present disclosure.

This affinity capture of secreted antibody product by the protein A coated beads, followed by washing, elution and regeneration steps can be carried out in a sequence of batch operations in a single settler or continuously in a sequence of settlers. In operation, the protein A beads will flow from one settler to the next settler in a truly counter-current or cross-flow operation with the cell culture broth or different buffers in each settler of embodiments of the present disclosure.

Example 11

Decanter/Cell Settler for In Situ Extraction of Secreted Organic Products from Cells Production and secretion of several fragrance and flavor compounds are being metabolically engineered into microbial yeast cells, such as *Saccharomyces cerevisiae*. Some of these compounds may be more toxic to the cells and can be extracted readily into an organic liquid to reduce the cellular toxicity as well as to increase the productivity of the yeast cells. Emulsions of organic liquid containing the secreted product and aqueous layer containing the productive microbial cells from the stirred tank bioreactor can be pumped into the inlet port of a compact cell settler device of this disclosure. Inside the quiet zones of the settler, the emulsion is separated easily into the organic layer floating on top and harvested via the top port and aqueous layer containing the live and productive cells settling to the bottom and recycled to the bioreactor via bottom port. Any cellular debris will fractionate into the organic layer and easily removed from the top of settler. Live and productive cells in the aqueous layers are returned to the bioreactor to increase the cell densities and productivity inside the perfusion bioreactor.

Example 12

In Vitro Expansion of Various Mammalian Cells, in a Compact Cell Settler Used as a Stand-Alone Perfusion Bioreactor Currently, the field of in vitro expansion of various mammalian cells such as stem cells and CAR-T cells is expanding rapidly with sterile single-use disposable culture bags as the bioreactors placed on rocking platform for mixing or inside a $CO_2$ incubator for pH control. Such bag bioreactors are increasingly operated in continuous perfusion mode to remove the accumulated waste metabolic by-products, such as ammonia and lactate, using microfiltration membranes as cell retention devices on the bag to maintain high cell viability during the expansion. However, during the prolonged perfusion operation, dead cells and cell debris accumulate in these bags and cannot be removed through the microfiltration membranes on the bag. The cell settler devices of this disclosure can be operated effectively as a stand-alone, air-lift bioreactors, operated in a continuous perfusion to bring in fresh nutrient and remove metabolic waste products, as well as to remove selectively any dead cells and cell debris. The bottom port can be used as an inlet for controlled mixture of multiple gases $CO_2$, $O_2$ and $N_2$ to maintain the desired pH and DO in the bioreactor. The rising air through the central portion entrains or carries up some cell culture liquid, provides a gentle mixing of the nutrients in the bioreactor, and exits at the top outlet, while the liquid is disengaged in the cylindrical portion of settler and is recycled over the conical settlers. The returning cell culture liquid can be sampled for continuous measurements of pH, DO, for inputs into computer controlling the inlet gas mixture and occasional sampling for cell density and viability as desired. After the desired cell expansion, concentrated live cells are collected via the bottom port by switching the gas flow to a cell collection bag. The major advantage of our cell settler/bioreactor is that it provides for a facile removal of dead cells and cell debris along with toxic metabolic waste by-products, resulting in a high cell density of live cells after in vitro expansion for autologous cell therapy.

Example 13

Continuous Separation of Precipitated and Concentrated Therapeutic Proteins

Several therapeutic proteins (e.g. insulin analog glargine and monoclonal antibodies) can be precipitated by adding simple salts (e.g. zinc chloride for glargine, or ammonium sulfate for antibodies), adjusting pH, and other solvents (e.g. m-cresol or other phenolics for glargine and ethanol for antibodies). This precipitation is a low-cost alternative to chromatography in the downstream purification processes for these therapeutic proteins. Currently, these precipitation steps are carried out in the batch mode, followed by centrifugation or decantation to remove the supernatant from the precipitant.

Using the separation devices of the present disclosure, a continuous separation process may be implemented. The protein rich harvest medium (after removing any cells by micro filtration or centrifugation or other methods) is input into a compact cell settler of this disclosure, along with other required chemicals, such as solvents, or salts in a pH-modifying solution, such as NaOH or HCl. The precipitation process will occur inside the settler and the protein-rich precipitant can be continuously removed in the bottom outlet, away from the protein-depleted supernatant, which is removed continuously from the top outlet.

Example 14

Ex Vivo Expansion of Mesenchymal Stromal/Stem Cells (MSCs) on Microcarrier Beads and Purification of Expanded Stem Cells MSCs are capable of ex vivo expansion in the presence of suitable growth medium and are commonly grown attached to surfaces, such as tissue culture flasks, petri dishes, roller bottles, cell cubes, and microcarrier beads. Attached growth on microcarrier beads (size ranging from 100 microns to 500 microns) is very easily scalable as they are suspended in stirred or agitated bioreactors, controlled for optimal growth conditions such as pH, temperature, dissolved oxygen concentration and nutrient concentrations. However, separation of expanded stem cells from the microcarriers is a challenge, requiring enzymatic detachment, washing off excess enzyme quickly, and separating the stem cells from microcarrier beads. These different steps are currently attempted using labor-intensive and contamination-prone batch processing steps. Each of these difficult steps can be accomplished more easily in the bioreactor/cell settler devices of this disclosure which may include sensor probes positioned within the cyclone housing. In one embodiment, the sensor probes comprise fluorescent probes to measure one or more of pH, dissolved oxygen (DO), glucose concentrations, temperature, and $CO_2$ levels within the cyclone housing. More specifically, within these settler devices: (i) the excess enzyme is very easily washed or removed via the top port by feeding in fresh nutrient medium via the bottom port while the slower-setting detached cells and fast-settling, freshly denuded microcarrier beads are held in circulation inside the settler, (ii) bare microcarrier beads (100-500 microns) will settle much faster than the stem cells (10-20 microns) and can be removed from the bottom port while the stem cells are circulated in suspension, and (iii) finally the expanded stem cells can be harvested via the bottom port at the desired concentration for subsequent cell therapy applications.

Example 15

Co-Culture of Stromal Cells on Microcarrier Beads to Secrete the Necessary Growth Factors to Support the In Vitro Expansion or Growth of Other Differentiated Cells, Such as T-Lymphocytes or Cardiomyocytes Growth and differentiation of pluripotent stem cells into cardiomyocytes or activated lymphocytes (CAR-T cells) require expensive growth factors to be supplemented to the growth bioreactor. This cost can be reduced by co-culturing the desired cells with engineered mesenchymal stem cells (MSCs) that secrete the desired growth factors into the growth medium. These growth factor secreting cells support the growth of other desired cells, such as CAR-T cells, cardiomyoctyes, etc. This co-culture can be effected inside the bioreactor/cell sorter combination devices of this disclosure, and the cost of production or expansion of such cells is significantly reduced. The expanded cells can be easily removed from the co-culture by feeding in fresh medium at a required flow rate to remove the expanded single cells or cell aggregates, while keeping larger, microcarrier beads inside the bioreactor/cell settler.

Example 16

Fractionation or Sorting of any Mixed-Cell Population, Such as from Bone Marrow, into Several Distinct Sub-Populations with Desirable or Undesirable Characteristics After loading any of the bioreactor/cell settler devices of the present disclosure with some initial bolus of a mixed cell population (such as bone marrow cells), we can feed in fresh nutrient medium at slow, step-wise increasing flow rates, such that the smallest cells (e.g. platelets, red blood cells, etc.) leave via top effluent stream at the lowest flow rates, followed by bigger cell types (lymphocytes, mononuclear cells, etc.) at increasingly higher flow rates, and then by the biggest cell types (such as macrophages, megakaryocytes, etc.) at the highest flow rates. By increasing the nutrient feed and the top effluent flow rates at slowly-increasing step-wise flow rates, relatively pure populations of a single desired cell type are obtained leaving the bioreactor/cell sorter device in a healthy cell culture growth medium so they can be propagated further for subsequent use.

Example 17

In Vitro Production of Universal Red Blood Cells

Novel genetic engineering methods are under development for directed differentiation of hematopoietic stem cells into erythroid cell lineage. Proerythroblast cells, the earliest committed stage in erhthropoiesis, are rather large (12-20 microns), up to three times larger than a normal erythrocyte. Polychromatophilic normoblasts, the subsequent stage in erythroid lineage, is smaller (12-15 microns) than the proerythroblast cells. Orthochromatophilic normoblast cells, the nucleated erythroid precursor cells, are still smaller (8-12 microns), followed by the still smaller mature enucleated red blood cells. (Geiler, C., et al., International Journal of Stem Cells, 9:53-59). Based on size fractionation capabilities of the bioreactor/cell sorter devices of this disclosure, all the larger precursor cells are retained, and only the smallest mature enucleated red blood cells are removed from the top effluent of the device, while all the larger precursor cells are continually expanding inside the bioreactor/cell sorter device.

Example 18

Large-Scale Platelet Production

Ex vivo expansion of high-ploidy megakaryocytic cells in controlled bioreactor culture conditions and their shearing off into smaller platelet cells is increasingly understood at a fundamental level (Panuganti, S., et al., Tissue Engineering Part A, 19:998-1014). As this understanding develops further, these necessary culture parameters can be obtained and controlled inside these bioreactor/cell sorter devices for growth and differentiation of megakaryocytic cells, while harvesting only the mature, sheared off smaller platelets via the top outlet from the settler.

To provide additional background, context, and to further satisfy the written description requirements of 35 U.S.C. § 112, the following references are incorporated by reference herein in their entireties: U.S. Pat. No. 5,624,580, U.S. Patent App. Pub. 2009/159523, U.S. Patent App. Pub. 2011/097800, U.S. Patent App. Pub. 2012/180662, U.S. Patent App. Pub. 2014/011270.

The foregoing examples of the present disclosure have been presented for purposes of illustration and description. These examples are not intended to limit the disclosure to the form disclosed herein. Consequently, variations and modifications commensurate with the teachings of the description of the disclosure, and the skill or knowledge of the relevant art, are within the scope of the present disclosure. The specific embodiments described in the examples provided herein are intended to further explain the best mode known for practicing the disclosure and to enable others skilled in the art to utilize the disclosure in such, or other, embodiments and with various modifications required by the particular applications or uses of the present disclosure. It is intended that the appended claims be construed to include alternative embodiments to the extent permitted by the prior art.

What is claimed is:

1. A settling device comprising:
    an upper conical portion with at least one port;
    a cylindrical portion;
    a lower conical portion with at least one port;
    a stack of cones located within the settling device, each cone of the stack of cones including a first opening and a second opening that is larger than the first opening, each of the first openings oriented towards one of the upper conical portion and the lower conical portion, the stack of cones generally centered around a longitudinal axis of the settling device; and
    a diffuser positioned within the setting device, the diffuser including a stem interconnected to a port of the at least one port of the lower conical portion and a ring extending from the stem.

2. The settling device of claim 1, wherein at least one cone of the stack of cones is comprised of a plastic and the settling device is disposable.

3. The settling device of claim 1, wherein the settling device further comprises a first flange engaged with a second flange.

4. The settling device of claim 1, wherein an interior surface of each cone of the stack of cones is oriented at an angle of between approximately 5 degrees to about 85 degrees relative to the longitudinal axis.

5. The settling device of claim 1, wherein the upper and lower conical portions taper along an arcuate path from a maximum diameter proximate to the cylindrical portion to a minimum diameter at respective upper and lower ends.

6. The settling device of claim 1, wherein the at least one port of the lower conical portion comprises:
    a first port that is aligned substantially concentrically with the longitudinal axis; and
    a second port that is offset from the longitudinal axis, wherein the stem of the diffuser is interconnected to the second port.

7. The settling device of claim 1, wherein an interior surface of each cone has a first radius of curvature proximate to the first opening and a second radius of curvature proximate to the second opening, wherein the second radius of curvature is different than the first radius of curvature.

8. The settling device of claim 1, wherein an aperture is formed in the ring of the diffuser to inject fluid into or withdraw fluid from the settling device through the port of the at least one port of the lower conical portion.

9. The settling device of claim 8, wherein at least one of the cones is provided in contact with the ring of the diffuser and the stack of cones is supported by the ring of the diffuser.

10. The settling device of claim 1, wherein the first opening of each cone of the stack of cones is oriented toward the lower conical portion.

11. The settling device of claim 1, further comprising a fluorescent probe to measure at least one of pH, dissolved oxygen, and dissolved CO2 within the settling device; and wherein
the lower conical portion is transparent or translucent.

12. The settling device of claim 1, further comprising a conduit interconnected to a port of the at least one port of the upper conical portion, the conduit including a free end positioned within an interior of an upper cone of the stack of cones.

13. A method of settling particles in a suspension, comprising:
introducing a liquid suspension of particles into a settling device which includes:
an upper conical portion with an upper port;
a cylindrical portion;
a lower conical portion with a first lower port and a second lower port;
a stack of cones located within the settling device, each cone of the stack of cones including a body with a first opening and a second opening that is larger than the first opening, each of the first openings oriented towards one of the upper conical portion and the lower conical portion, the stack of cones generally centered around a longitudinal axis of the settling device; and
a diffuser positioned within the setting device, the diffuser including a stem interconnected to the second lower port of the lower conical portion and a ring extending from the stem;
collecting a clarified liquid from the upper port; and
collecting a concentrated liquid suspension from the first lower port.

14. The method of claim 13, wherein the liquid suspension comprises at least one of a recombinant cell suspension, an alcoholic fermentation, a suspension of solid catalyst particles, a municipal waste water, industrial waste water, mammalian cells, bacterial cells, yeast cells, plant cells, algae cells, plant cells, mammalian cells, murine hybridoma cells, stem cells, CAR-T cells, red blood precursor and mature cells, cardiomyocytes, yeast in beer, and eukaryotic cells.

15. The method of claim 13, wherein the liquid suspension comprises at least one of:
(a) recombinant microbial cells selected from at least one of *Pichia pastoris, Saccharomyces cerevisiae, Kluyveromyces lactis, Aspergillus niger, Escherichia coli,* and *Bacillus subtilis*; and
(b) one or more of microcarrier beads, affinity ligands, and surface activated microspherical beads.

16. The method of claim 13, wherein introducing a liquid suspension comprises directing the liquid suspension from a plastic disposable bioreactor bag into the settling device.

17. The method of claim 13, wherein the clarified liquid collected comprises at least one of biological molecules, organic or inorganic compounds, chemical reactants, and chemical reaction products.

18. The method of claim 13, wherein the clarified liquid collected comprises at least one of hydrocarbons, polypeptides, proteins, alcohols, fatty acids, hormones, carbohydrates, antibodies, glycoproteins, terpenes, isoprenoids, polyprenoids, and beer.

19. The method of claim 13, wherein the clarified liquid collected comprises at least one of biodiesel, insulin, brazzein, antibodies, growth factors, colony stimulating factors, and erythropoietin (EPO).

20. The method of claim 13, wherein introducing a liquid suspension of particles into the settling device comprises pumping the liquid suspension through the second lower port of the lower conical portion and through an aperture formed in the ring of the diffuser.

21. The method of claim 13, further comprising measuring pH, dissolved oxygen (DO), and dissolved $CO_2$ within the settling device with a sensor positioned within the settling device.

22. The method of claim 21, further comprising adjusting one or more of pH and DO within the settling device by introducing at least one of $O_2$, $CO_2$, and $N_2$ into the settling device.

23. The method of claim 13, further comprising withdrawing fluid from the settling device through a conduit interconnected to a second upper port of the upper conical portion, the conduit including a free end positioned between the first opening and the second opening of an uppermost cone of the stack of cones.

* * * * *